United States Patent
Furet et al.

(10) Patent No.: US 9,403,827 B2
(45) Date of Patent: Aug. 2, 2016

(54) SUBSTITUTED PURINONE COMPOUNDS

(71) Applicants: Pascal Furet, Thann (FR); Vito Guagnano, Basel (CH); Philipp Holzer, Sissach (CH); Joerg Kallen, Basel (CH); Robert Mah, Muttenz (CH); Keiichi Masuya, Basel (CH); Achim Schlapbach, Basel (CH); Andrea Vaupel, Riehen (CH)

(72) Inventors: Pascal Furet, Thann (FR); Vito Guagnano, Basel (CH); Philipp Holzer, Sissach (CH); Joerg Kallen, Basel (CH); Robert Mah, Muttenz (CH); Keiichi Masuya, Basel (CH); Achim Schlapbach, Basel (CH); Andrea Vaupel, Riehen (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/762,037

(22) PCT Filed: Jan. 21, 2014

(86) PCT No.: PCT/IB2014/058433
§ 371 (c)(1),
(2) Date: Jul. 20, 2015

(87) PCT Pub. No.: WO2014/115077
PCT Pub. Date: Jul. 31, 2014

(65) Prior Publication Data
US 2015/0353551 A1    Dec. 10, 2015

Related U.S. Application Data

(60) Provisional application No. 61/755,009, filed on Jan. 22, 2013.

(51) Int. Cl.
*A61K 31/522*    (2006.01)
*C07D 473/28*    (2006.01)

(52) U.S. Cl.
CPC ............ *C07D 473/28* (2013.01); *A61K 31/522* (2013.01)

(58) Field of Classification Search
CPC .......................... C07D 473/28; A61K 31/522
See application file for complete search history.

(56) References Cited

U.S. PATENT DOCUMENTS

| | | | |
|---|---|---|---|
| 3,829,420 A | 8/1974 | Inaba et al. | |
| 3,865,827 A | 2/1975 | Yamamoto et al. | |
| 3,923,710 A | 12/1975 | Ishizumi et al. | |
| 4,099,002 A | 7/1978 | Inaba et al. | |
| 4,258,187 A | 3/1981 | Middleton | |
| 4,335,127 A | 6/1982 | Vandenberk et al. | |
| 4,695,633 A | 9/1987 | Berneth et al. | |
| 6,479,499 B1 | 11/2002 | Kuo et al. | |
| 6,734,302 B2 | 5/2004 | Kong et al. | |
| 7,541,354 B2 | 6/2009 | Fancelli et al. | |
| 8,101,644 B2 | 1/2012 | Kai et al. | |
| 8,222,288 B2 | 7/2012 | Wang et al. | |
| 8,440,693 B2 | 5/2013 | Berghausen et al. | |
| 8,969,341 B2 * | 3/2015 | Furet ................... | C07D 487/04 514/234.2 |
| 2003/0153580 A1 | 8/2003 | Kong et al. | |
| 2006/0069085 A1 | 3/2006 | Zhao et al. | |
| 2008/0153791 A1 | 6/2008 | Wilckens | |
| 2009/0163545 A1 | 6/2009 | Goldfarb | |
| 2010/0160356 A1 | 6/2010 | Heinrich et al. | |
| 2010/0210632 A1 | 8/2010 | Kai et al. | |
| 2011/0183939 A1 | 7/2011 | Kai et al. | |
| 2011/0230457 A1 | 9/2011 | Berghausen et al. | |
| 2011/0301133 A1 | 12/2011 | Wu et al. | |
| 2012/0065210 A1 | 3/2012 | Chu et al. | |
| 2013/0245036 A1 | 9/2013 | Berghausen et al. | |
| 2013/0281396 A1 | 10/2013 | McLure et al. | |
| 2013/0281473 A1 | 10/2013 | Berghausen et al. | |
| 2013/0317024 A1 | 11/2013 | Cotesta et al. | |
| 2014/0011798 A1 | 1/2014 | Furet et al. | |
| 2014/0135306 A1 | 5/2014 | Buschmann et al. | |

FOREIGN PATENT DOCUMENTS

| | | |
|---|---|---|
| EP | 1657238 A1 | 5/2006 |
| EP | 2 143 713 A1 | 1/2010 |
| JP | 45-16950 A | 6/1970 |
| JP | 46-15500 A | 4/1971 |
| JP | 57021388 | 2/1982 |
| JP | 2001302515 A | 10/2001 |
| JP | 2005-511766 A | 4/2005 |
| JP | 2006-524228 | 10/2006 |
| JP | 2014-533745 | 12/2014 |
| WO | 93/04047 A1 | 3/1993 |

(Continued)

OTHER PUBLICATIONS

No Author Listed, National Cancer Institute. "Drugs Approved for Leukemia." © 2013. Available from: http://www.cancer.gov/cancertopics/druginfo/leukemia/print >.

Richter et al., An Optimised Small-Molecule Stabiliser of the 14-3-3-PMA2 Protein-Protein Interaction. Chem. Eur. J. 2012:18(21):6520-7.

Sun et al., Single-Nucleotide Polymorphisms in p53 Pathway and Aggressiveness of Prostate Cancer in a Caucasian Population. Clin. Cancer Res. 2010;16:5244-51.

(Continued)

*Primary Examiner* — Golam M M Shameem
(74) *Attorney, Agent, or Firm* — Qian Zhang

(57) ABSTRACT

The invention relates to compounds of formula (I): (I) as described herein, pharmaceutical preparations comprising such compounds, uses and methods of use for such compounds in the treatment of a disorder or a disease mediated by the activity of as MDM2 and/or MDM4, and combinations comprising such compounds.

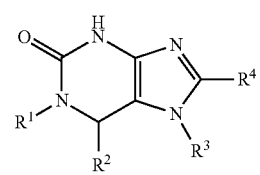

(I)

10 Claims, No Drawings

(56) References Cited

FOREIGN PATENT DOCUMENTS

| WO | 95/19362 A1 | 7/1995 |
|---|---|---|
| WO | 98/19362 A1 | 7/1995 |
| WO | 98/01467 A2 | 1/1998 |
| WO | 98/45276 A2 | 10/1998 |
| WO | 00/66560 A1 | 11/2000 |
| WO | 02/12242 A2 | 2/2002 |
| WO | 03/051359 | 6/2003 |
| WO | 03/062392 A2 | 7/2003 |
| WO | 03/095625 A2 | 11/2003 |
| WO | 03/101985 A1 | 12/2003 |
| WO | 2004/014916 | 2/2004 |
| WO | 2004/014916 A1 | 2/2004 |
| WO | 2004/094421 A1 | 11/2004 |
| WO | 2004/094429 A1 | 11/2004 |
| WO | 2004/096134 A2 | 11/2004 |
| WO | 2005/027882 A1 | 3/2005 |
| WO | 2005/051922 A1 | 6/2005 |
| WO | 2005/110996 A1 | 11/2005 |
| WO | 2005/117876 A1 | 12/2005 |
| WO | 2006/024837 A1 | 3/2006 |
| WO | 2006/074262 A1 | 7/2006 |
| WO | 2006/097337 A1 | 9/2006 |
| WO | 2006/100038 A1 | 9/2006 |
| WO | 2006/136606 A2 | 12/2006 |
| WO | 2007/068637 A1 | 6/2007 |
| WO | 2007/096334 A1 | 8/2007 |
| WO | 2007/144384 A1 | 12/2007 |
| WO | 2008/034039 A2 | 3/2008 |
| WO | 2008/045529 A1 | 4/2008 |
| WO | 2008/120725 A1 | 10/2008 |
| WO | 2008/130614 A2 | 10/2008 |
| WO | 2010/007116 A2 | 1/2010 |
| WO | 2010/035727 A1 | 4/2010 |
| WO | 2010/047956 A1 | 4/2010 |
| WO | 2010/141738 A2 | 12/2010 |
| WO | 2011/076786 A1 | 6/2011 |
| WO | 2011/161031 A1 | 12/2011 |
| WO | 2012/034954 A1 | 3/2012 |
| WO | 2012/046030 A2 | 4/2012 |
| WO | 2012/065022 A2 | 5/2012 |
| WO | 2012/151512 A2 | 11/2012 |
| WO | 2012/174487 A2 | 12/2012 |
| WO | 2012/175487 A2 | 12/2012 |
| WO | 2012/175520 A1 | 12/2012 |
| WO | 2013/027168 A1 | 2/2013 |
| WO | 2013/033268 A2 | 3/2013 |
| WO | 2013/033270 A2 | 3/2013 |
| WO | 2013/080141 A1 | 6/2013 |
| WO | 2013/097052 A1 | 7/2013 |
| WO | 2013/111105 A1 | 8/2013 |
| WO | 2013/156869 A1 | 10/2013 |
| WO | 2013/158952 A1 | 10/2013 |
| WO | 2013/175281 A1 | 11/2013 |
| WO | 2013/175417 A1 | 11/2013 |
| WO | 2014/115077 A1 | 7/2014 |

OTHER PUBLICATIONS

Vanotti et al., Cdc7 Kinase Inhibitors: Pyrrolopyrimidinones as Potential Antitumor Agents. 1. Synthesis and Structure-Activity Relationships. Journal of Medicinal Chemistry. 2008;51:487-501.

Wade et al., Targeting Mdm2 and Mdmx in Cancer Therapy: Better Living through Medicinal Chemistry? Mol. Cancer Res. 2009;7:1-11.

Wang et al., Benzimidazole-2-one: A novel anchoring principle for antagonizing p53-Mdm2. Bioorganic & Medicinal Chemistry. 2013;21:3982-95.

Westphal The formation of pyrrolo[3,4-c]pyrazoles. Journal for Practical Chemistry. 1969;311:379-84.

Gein et al, "Synthesis and analgesic activity of 5-aryl-4-heteroyl-3-hydroxy-1-(2-thiazolyl)-3-pyrrolin- 2-ones and their derivatives" Perm State Pharmaceutical Academy, Perm, 614990, Russia; Pharmaceutical Chemistry Journal (2014), 47(10),539-543.

Search Report generated on Oct. 8, 2012 against databases including CAS Registry, CAPlus, Derwent World Patents Index, MarPat, Questel-Orbit Pharm, Merged Markush Service—MMS and Reaxys.

Acharya, B.P. et al., "Friedel-Crafts Acylation with 2-Isocyanatobenzoyl Chlorides: The Structure of the Intermediate Complex," Journal of Chemical Research, Synopses, (4):96-7 (1987)[Abstract only].

Bahloul, A. et al., "1,3-Dipolar Cycloaddition of Diarylnitrilimines with 4-Arylidene-1,2-Diphenyl-1,4-Dihydro-3(2H)-Isoquinolin-3-Ones," Journal de la Societe Marocaine de Chimie, 2(1):12-17 (French)(1993)[Abstract only].

Chen, R. et al., "Ytterbium(III) Triflate-Catalyzed Stereoselective Synthesis of Beta-lactams via [2+2] Cyclocondensation in Ionic Liquid," Synthetic Communications, 36(21):3167-3174, Taylor & Francis Group, LLC (English)(2006).

De Luca et al., "3D Pharmacophore Models for 1,2,3,4-Tetrahydroisoquinoline Derivatives Acting as Anticonvulsant Agents" Arch. Pharm. Chem. Life Sci., 2006, 339, 388-400.

Dietz, G. et al.; "Synthesis and Conversion of 3,4-Dihydroquinazolin-4-ols. Part 2: Conversion of 3,4-Dihydroquinazolin-4-ols;" Direktionsber. Forsch. Entwickl., VEB Pharm. Komb. Germed Dresden, Ger. Dem. Rep.; Pharmazie; 35(12):751-5 (German)(1980)[Abstract only].

Dudkina, Anna S. et al. "Small Molecule Protein-Protein Inhibitors for the p53-MDM2 Interaction", Current Topics in Medicinal Chemistry, 2007, 7, pp. 952-960.

Ishiwaka, N. et al., "o-Aminobenzophenone Derivatives. V. Reactions of 2-Amino-5-Chloro-Benzophenone with Isocyanates and Isothiocyanates," Kagaku Zasshi, 90(9):917-20 (Japanese)(1969)[Abstract only].

Ishiwaka, N. et al., "Reaction of 2-Amino-5-Chlorobenzophenone with P-Substituted Phenyl Isocyanates," Kagaku Zasshi, 91(10):994-7 (Japanese)(1970)[Abstract only].

Ivanov et al., Polyphosphoric acid-induced construction of quinazolinone skeleton from 1-(3,4-dimethoxyphenyl)-3-phenylurea and carboxylic acids. Heterocycles. May 12, 2006;68(7):1443-9.

Ivanov, I., "Synthesis of 6,7-Dimethoxy-3,4-Diphenyl-2(1H)-Quinazolinone from 1-(3,4-Dimethoxyphenyl)Urea and Benzoic Acid in Polyphosphoric Acid," Molbank M492/1-M492/2 (English)(2006)[Abstract only].

Mollov, N.M. et al., "Internal Alpha-Amidoalkylation Leading to 1,4-Dihydro-3(2H)-Isoquinolinones," Acta Chimica Academiae Scientiarum Hungaricae, 98(3):315-19 (English)(1978).

Mollov, N.M. et al., "Reactivity of Adducts Obtained from Arylacetyl Chloride and Aromatic Schiff Bases," Izvestiya po Khimiya, 10(4):616-20 (English)(1977).

Mollov, N.M. et al., "Synthesis of 3(2H)-isoquinolinones by Means of Inner Alpha-Amidoalkylation," Doklady Bolgarskoi Akademii Nauk, 28(8):1055-7 (English)(1975)[Abstract only].

Mumm, O. et al., "Diacylamides," Berichte der Deutschen Chemischen Gesellschaft, 48:379-91 (1915)[Abstract only].

Pfeiffer, P. et al., "Autoxidation Phenomena in the Anils of the Indandione Series. II," Journal fuer Praktische Chemie (Leipzig), 159:13-35 (1941)[Abstract and Article].

Pfeiffer, P. et al., "Autoxidation Phenomena. VI," Justus Liebigs Annalen der Chemie, 563:73-85 (1949)[Abstract and Article].

Pfeiffer, P. et al., "Autoxidation Reactions. VII," Justus Liebigs Annalen der Chemie, 581:149-59 (1953)[Abstract and Article].

Richter, D., "Anthraquinone Coloring Matters: Ruberythric Acid," Journal of the Chemical Society, 1701-3 (1936).

Richter, P. et al., "Synthesis of Derivatives of 2-Hydrazino-1,4- or 3,4-Dihydroquinazolines," Pharmazie, 45(10):721-4 (German)(1990)[Abstract only].

Schonberg, A. et al., "Autoxidation Effects in the Indone Series," Naturwissenschaften, 24:620 (1936)[Abstract only].

Schonberg, A. et al., "Autoxidation Phenomena and Valency Tautomerism in the Indone Series," Journal of the Chemical Society, 109-12 (1937).

Shangary, Sanjeev et al., "Targeting the MDM2-p53 Interaction for Cancer Therapy", Clin. Cancer Res., 2008, 14, 5318-5324.

Venkov, A. et al., "An Improved Synthesis of N-Substituted 1-Aryl-3-Oxo-1,2,3,4-Tetrahydroisoquinolines," Synthesis, 216-17, Stuttgart, New York (English)(1982).

(56) References Cited

OTHER PUBLICATIONS

Ventsov, A. et al., "Synthesis of N-Substituted 1,4-Dihydro-3(2H)-Isoquinolinones from 3,4,5-Trimethoxyphenylacetyl chloride and Schiff Bases," Bolgarskoi Akademii Nauk, 34(10):1405-7 (English)(1981)[Abstract only].

Yamamoto, M. et al., "Synthetic Studies on Quinazoline Derivatives. II. The Reactions of 2-Trichloro- and 2-Trifluoroacetamidobenzophenones with Primary Amines," Chemical & Pharmaceutical Bulletin, 29(8):2135-56 (English)(1981).

Zhang, Y. et al., "Superacid-Promoted Reactions of N-Acyliminium Ions: An Effective Route to Substituted 3-Oxo-1,2,3,4-Tetrahydroisoquinolines and Related Products," Synthesis (11):1775-1780 (English)(2006).

Zin'kovskaya, V.R. et al., "Ring-chain transformations involving the carbonyl group. XVI. Amides of 2-benzoylphenyl-Alpha,Alpha-dimethylacetic acid," Latvijas PSR Zinatnu, Akademijas Vestis, Kimijas Serija, (1)65-8 (Russian)(1976)[Abstract only].

Sheng, R. et al, Pharmacophore model construction of p53-MDM2 binding inhibitors, Acta Physico-Chimica Sinica, Aug. 6, 2007, vol. 23, No. 11,p. 1815-1820.

Aebi, A. et al, Pharmaceutica Acta Helvetiae, vol. 38, Issue: 7-8, pp. 616-622, Journal, 1963.

Shams El-Dine, S. A et al Pharmazie, vol. 56, Issue: 12, pp. 933-937, Journal, 2001.

Chaudhari, P.V., Oriental Journal of Chemistry (2012), 28(1), 507-512.

Journal of Enzyme Inhibition and Medicinal Chemistry (2011), 26(4), 472-479.

J. D. Akbari et al.: Indian Journal of Chemistry, Section B: Organic Chemistry Including Medicinal Chemistry (2008), 47B(3), 477-480.

Raj et al.: Organic Chemistry: An Indian Journal (2007), 3(4),176-179.

Ahmed Kamal et al.: Expert opinion on therapeutic patents 2012, vol. 22, No. 2, pp. 95-105, XP055107028.

Chung et al., Fragment-based discovery of bromodomain inhibitors part 1: inhibitor binding modes and implications for lead discovery. J Med Chem. Jan. 26, 2012;55(2):576-86.

Filippakopoulos et al., Benzodiazepines and benzotriazepines as protein interaction inhibitors targeting bromodomains of the BET family. Bioorg Med Chem. Mar. 15, 2012;20(6):1878-86.

Filippakopoulos et al., Selective inhibition of BET bromodomains. Nature. Dec. 23, 2010;468(7327):1067-73.

Hackam et al., Translation of research evidence from animals to humans. JAMA. Oct. 11, 2006;296(14):1731-2.

Jordan, Tamoxifen: a most unlikely pioneering medicine. Nat Rev Drug Discov. Mar. 2003;2(3):205-13.

Wu et al., The double bromodomain-containing chromatin adaptor Brd4 and transcriptional regulation. J Biol Chem. May 4, 2007;282(18):13141-5.

Andreichikov et al., Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine. Journal of Organic Chemistry 1986;22(8):1572-7.

Dohrn et al., Berichte der Deutschen Chemischen Gesellschaft [Abteilung] B: Abhandlungen. 1931;64B:2863-5.

Gein et al., Reactions of 4-Acyl-1-alkoxyaryl-5-aryl-3-hydroxy-2,5-dihydro-1 H-pyrrol-2-ones with Nucleophilic Reagents. Russian Journal of Organic Chemistry. 2011;47(1):95-9.

Gein et al., 5-Membered 2,3-Dioxoheterocyclic Compounds. Journal of General Chemistry. 1993;63(10):2324-8.

Lee et al., Novel Pyrrolopyrimidine-Based alpha-Helix Mimetics: Cell Permeable Inhibitors of Protein-Protein Interactions. Journal of the American Chemical Society. 2010;133:676-9.

Miyazaki et al., Lead optimization of novel p53-MDM2 interaction inhibitors possessing dihydroimidazothiazole scaffold. Bioorganic and Medicinal Chemistry Letters. 2013;23:728-32.

No Auhtor Listed, WedMD "Leukemia." Available from: <http://www.webmd.com/cancer/tc/leukemia-prevention?print=true#> @2010.

No Author Listed, American Cancer Society. "Leukemia—Acute Myeloid (Myelogenous)." © 2013. Available from: <http://www.cancer.org/cancer/leukemia-acutemyeloidaml/detailedguide/leukemia-acute-myeloid-myelogenous-what-is-aml >.

No Author Listed, Mayo Clinic "Leukemia Medications." Available from: <http://www.drugs.com/condition/leukemia.html> @2013.

\* cited by examiner

SUBSTITUTED PURINONE COMPOUNDS

CROSS-REFERENCE TO RELATED APPLICATIONS

This application is a 35 USC 371 National Stage Filing of International Application No. PCT/IB2014/058433, filed Jan. 21, 2014, which claims priority under 35 USC 119(e) to U.S. Provisional Application No. 61/755,009, filed Jan. 22, 2013.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION BY REFERENCE OF MATERIAL SUBMITTED ON A COMPACT DISC

Not Applicable

BACKGROUND OF THE INVENTION

The present invention relates to novel imidazolo-pyrimidinone compounds, capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor suppressor. "MDM2" (originally from the oncogene "murine double minute 2") refers both to the name of the gene as well as the protein encoded by that gene. MDM2 protein functions both as an E3 ubiquitin ligase that recognizes the N-terminal transactivation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to cancers such as tumors, leukemias or other proliferative diseases.

WO2011/076786 discloses isoquinolinone and quinazolinone compounds as inhibitors of the interaction between p53 and MDM2 and/or 4.

There is a need for new drugs that are capable of interfering with the interaction between p53 and MDM2 or especially oncogenic variants thereof and that thus allow p53 to exert its beneficial effect against uncontrolled tumor growth, allowing it e.g. to accumulate, to arrest the cell cycle and/or to cause apoptosis of affected cells.

BRIEF SUMMARY OF THE INVENTION

It has now been found that a novel class of imidazolopyrimidinone compounds shows inhibition of the MDM2/p53 and/or MDM4/p53 interaction (this term including in particular Hdm2/p53 and Hdm4/p53 interaction), and in particular potent inhibition of the MDM2/p53 interaction. The corresponding compounds thus represent a novel type of compound that are useful in the treatment of a number of disorders, such as proliferative diseases, especially cancer. The invention relates therefore to these compounds as drugs as well as to the other inventive embodiments indicated herein.

Particularly interesting compounds of the invention herein are highly potent in the p53-Hdm2 inhibition (TR-FRET) Assay described herein. Compounds of particular interest possess favourable pharmacokinetic properties. They should be non-toxic and demonstrate few side-effects. Furthermore, the ideal drug candidate will exist in a physical form that is stable, non-hygroscopic and easily formulated.

DETAILED DESCRIPTION OF THE INVENTION

According to a first aspect of the invention there is provided a compound of formula (I) or a salt thereof,

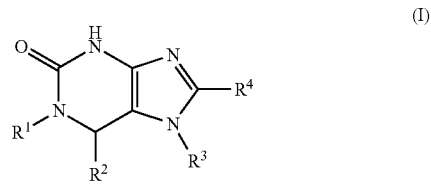

(I)

wherein
R$^1$ is
(a) a phenyl substituted with one to five substituents each independently selected from halo, (C$_1$-C$_4$)alkyl, or —O—(CH$_2$)$_n$—N(CH$_3$)$_2$, wherein n is 1 or 2; or
(b) a 6-oxo-1,6-dihydropyridin-3-yl having Formula (Ia) or a 2-oxo-1,2-dihydropyridin-3-yl having Formula (Ib),

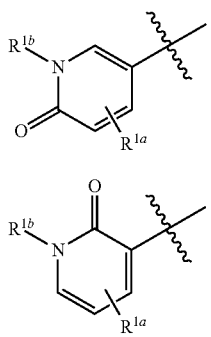

wherein $R^{1a}$ is H, halo or $(C_1-C_4)$alkyl, and $R^{1b}$ is H, $(C_1-C_4)$alkyl, —$(CH_2)_m$—$N(CH_3)_2$, or —$(CH_2)_m$—$OR^{1c}$, where $R^{1c}$ is H or $(C_1-C_4)$alkyl, and m is 1 or 2;

$R^2$ is a phenyl substituted with one substituent in the para position selected from chloro, fluoro, trifluoromethyl, methyl and cyano and optionally one additional substituent selected from halo, and $(C_1-C_4)$alkyl-, optionally substituted with $(C_1-C_4)$alkoxy;

$R^3$ is selected from isopropyl, cyclopropyl, isobutyl, cyclobutyl and cyclopentyl; and $R^4$ is halo, —$(CH_2)_q$-pyridyl, —$(CH_2)_q$-pyrimidyl, —$(CH_2)_q$-phenyl, where said pyridyl, said pyrimidyl, and said phenyl moieties are optionally substituted with one, two or three substituents each independently selected from halo, $(C_1-C_4)$alkoxy, cyano, —$NH_2$, $(C_1-C_4)$alkyl-NH—, $((C_1-C_4)$alkyl$)_2$-N—, —$(CH_2)$—OH, —$C(O)$—$NH_2$, —$C(O)$—$NH$—$(C_1-C_4)$alkyl, —$C(O)$—$N((C_1-C_4)$alkyl$)_2$, —$C(O)$—$NH$—$(CH_2)_p$—OH, —$(CH_2)$—$NH_2$, —$(CH_2)$—$NH$—$C(O)CH_3$, or —$(CH_2)$—$NH$—$C(O)H$, p is 1 or 2, and q is 0 or 1.

Unless specified otherwise, the term "compounds of the present invention" refers to compounds of formula (I) and subformulae thereof (add other additional genus structures as necessary), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

For example, a "compound of the present invention" or a "compound of formula (I)" can exist in tautomeric forms when $R^{1b}$ is H. Where an embodiment is directed to one tautomer, the embodiment includes all possible tautomeric forms.

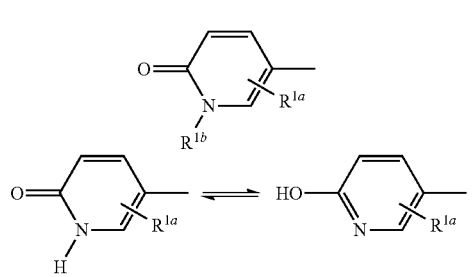

Various embodiments of the invention are described herein. It will be recognized that features specified in each embodiment may be combined with other specified features to provide further embodiments.

Described below are a number of embodiments (E) of the first aspect of the invention, where for convenience E1 is identical thereto.

E1 A compound of formula (I) as defined above or a salt thereof.

E2 A compound according to E1 wherein $R^1$ is a phenyl substituted with one to five substituents each independently selected from halo, $(C_1-C_4)$alkyl, or —O—$(CH_2)_n$—$N(CH_3)_2$, wherein n is 1 or 2.

E3 A compound according to either of E1 or E2 wherein $R^1$ is a phenyl substituted with one or two substituents each independently selected from halo, $(C_1-C_4)$alkyl, or —O—$(CH_2)_n$—$N(CH_3)_2$, wherein n is 1 or 2.

E4 A compound according to any of E1 to E3 wherein $R^1$ is a phenyl substituted with one or two substituents each independently selected from halo or $(C_1-C_4)$alkyl.

E5 A compound according to any of E1 to E4 wherein $R^1$ is a phenyl substituted with one or two substituents each independently selected from chloro, fluoro or methyl.

E6 A compound according to E1 wherein $R^1$ is a 6-oxo-1,6-dihydropyridin-3-yl having Formula (Ia) or a 2-oxo-1,2-dihydropyridin-3-yl having Formula (Ib),

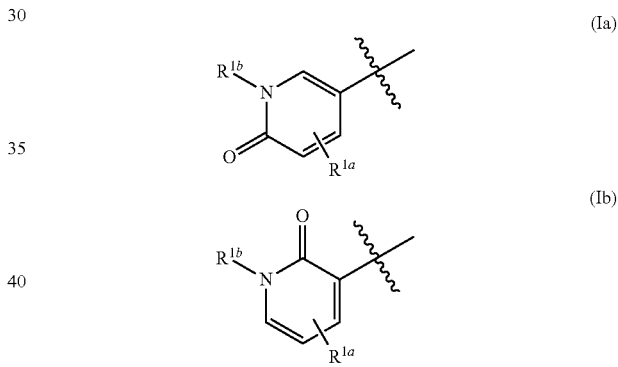

wherein $R^{1a}$ is H, halo or $(C_1-C_4)$alkyl, and $R^{1b}$ is H, $(C_1-C_4)$alkyl, —$(CH_2)_m$—$N(CH_3)_2$, or —$(CH_2)_m$—$OR^{1c}$, where $R^{1c}$ is H or $(C_1-C_4)$alkyl, and m is 1 or 2.

E7 A compound according to either of E1 or E6 wherein $R^1$ is a 6-oxo-1,6-dihydropyridin-3-yl having formula (Ia)

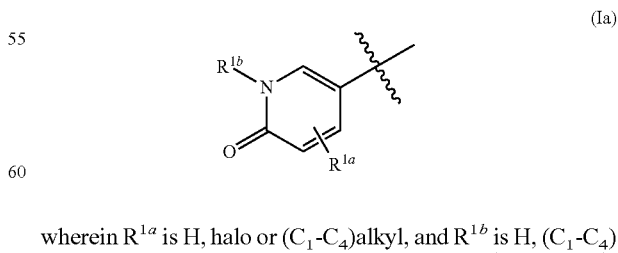

wherein $R^{1a}$ is H, halo or $(C_1-C_4)$alkyl, and $R^{1b}$ is H, $(C_1-C_4)$alkyl, —$(CH_2)_m$—$N(CH_3)_2$, or —$(CH_2)_m$—$OR^{1c}$, where $R^{1c}$ is H or $(C_1-C_4)$alkyl, and m is 1 or 2.

E8 A compound according to either of E1 or E6 wherein $R^1$ is 2-oxo-1,2-dihydropyridin-3-yl having Formula (Ib)

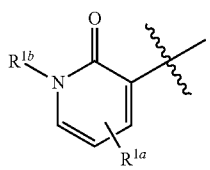

(Ib)

wherein $R^{1a}$ is H, halo or $(C_1-C_4)$alkyl, and $R^{1b}$ is H, $(C_1-C_4)$alkyl, $-(CH_2)_m-N(CH_3)_2$, or $-(CH_2)_m-OR^{1c}$, where $R^{1c}$ is H or $(C_1-C_4)$alkyl, and m is 1 or 2.

E9 A compound according to E1 or E6 to E8 wherein $R^{1a}$ is halo and $R^{1b}$ is H or $(C_1-C_4)$alkyl.

E10 A compound according to any of E1 to E9 wherein $R^2$ is a phenyl substituted with one substituent in the para position selected from chloro, fluoro, trifluoromethyl, methyl and cyano and optionally one additional substituent selected from halo, and $(C_1-C_4)$alkyl-.

E11 A compound according to any of E1 to E10 wherein $R^2$ is a phenyl substituted with one substituent in the para position selected from chloro, fluoro, and cyano and optionally one additional substituent selected from halo, and $(C_1-C_4)$alkyl-.

E12 A compound according to any of E1 to E11 wherein $R^2$ is selected from p-chlorophenyl, p-cyanophenyl, o-methyl-p-chlorophenyl, p-fluoro-m-chlorophenyl or m-fluoro-p-chlorophenyl.

E13 A compound according to any of E1 to E12 wherein $R^2$ is selected from p-chlorophenyl, o-methyl-p-chlorophenyl or m-fluoro-p-chlorophenyl.

E14 A compound according to any of E1 to E13 wherein $R^3$ is isopropyl.

E15 A compound according to any of E1 to E14 wherein $R^4$ is halo.

E16 A compound according to any of E1 to E14 wherein $R^4$ is selected from $-(CH_2)_q$-pyridyl, $-(CH_2)_q$-pyrimidyl, or $-(CH_2)_q$-phenyl, where said pyridyl, said pyrimidyl, and said phenyl moieties are optionally substituted with one or two substituents each independently selected from halo, $(C_1-C_4)$alkoxy, cyano, $-NH_2$, $(C_1-C_4)$alkyl-NH—, $((C_1-C_4)$alkyl)$_2$-N—, $-(CH_2)$—OH, $-C(O)-NH_2$, $-C(O)-NH-(C_1-C_4)$alkyl, $-C(O)-N((C_1-C_4)$alkyl)$_2$, $-C(O)-NH-(CH_2)_p$—OH, $-(CH_2)-NH_2$, $-(CH_2)-NH-C(O)CH_3$, or $-(CH_2)-NH-C(O)H$, where p is 1 or 2, and q is 0 or 1.

E17 A compound according to any of E1 to E14 and E16 wherein $R^4$ is selected from $-(CH_2)_q$-pyridyl, $-(CH_2)_q$-pyrimidyl, or $-(CH_2)_q$-phenyl, where said pyridyl, said pyrimidyl, and said phenyl moieties are optionally substituted with one or two substituents each independently selected from halo, $(C_1-C_4)$alkoxy, cyano, $-NH_2$, $((C_1-C_4)$alkyl)$_2$-N—, $-(CH_2)$—OH, $-C(O)-NH-(C_1-C_4)$alkyl, $-C(O)-N((C_1-C_4)$alkyl)$_2$, or $-C(O)-NH-(CH_2)_p$—OH where p is 1 or 2, and q is 0 or 1.

E18 A compound according to any of E1 to E14 and E16 to E17 wherein $R^4$ is selected from $-(CH_2)_q$-pyridyl, $-(CH_2)_q$-pyrimidyl, or $-(CH_2)_q$-phenyl, where said pyridyl, said pyrimidyl, and said phenyl moieties are optionally substituted with one or two substituents each independently selected from $(C_1-C_4)$alkoxy, $((C_1-C_4)$alkyl)$_2$-N—, $-C(O)-NH-(C_1-C_4)$alkyl, or $-C(O)-N((C_1-C_4)$alkyl)$_2$ where q is 0 or 1.

E19 A compound according to any of E1 to E14 and E16 to E18 wherein $R^4$ is selected from $-(CH_2)_q$-pyrimidyl or $-(CH_2)_q$-phenyl, where said pyrimidyl, and said phenyl moieties are substituted with one or two substituents as defined herein.

E20 A compound according to any of E1 to E14 and E16 to E19 wherein $R^4$ is selected from $-(CH_2)_q$-pyrimidyl, where said pyrimidyl moiety is substituted with one or two substituents as defined herein.

E21 A compound according to any of E1 to E14 and E16 to E19 wherein $R^4$ is selected from $-(CH_2)_q$-phenyl, where said phenyl moiety is substituted with one or two substituents as defined herein.

E22 A compound according to any of E1 to E14 and E16 to E21 wherein q is 0.

E23 A compound according to any of E1 to E14, E16 to E19 and E22 wherein $R^4$ is selected from

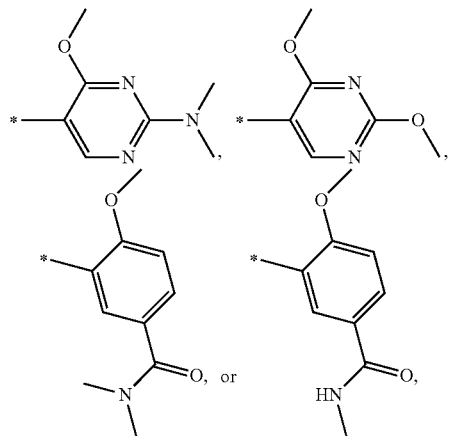

where * indicates the point of attachment to the remainder of the molecule.

E24 A compound according to any of E1 to E14, E16 to E20 and E22 to E23 wherein $R^4$ is selected from

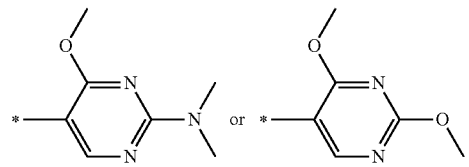

where * indicates the point of attachment to the remainder of the molecule.

E25 A compound according to any of E1 to E14, E16 to E19 and E21 to E23 wherein $R^4$ is selected from

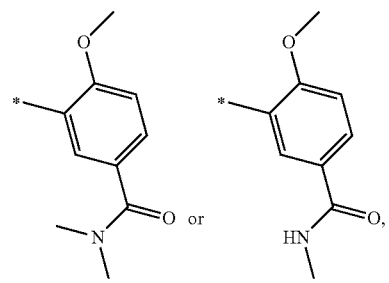

E26 A compound according to any of E1 to E25 wherein the compound of formula (I) has the stereochemistry shown in formula (Ic):

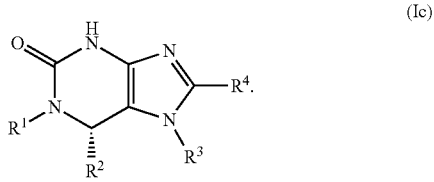

(Ic)

E27 A compound according to any of E1 to E25 wherein the compound of formula (I) has the stereochemistry shown in formula (Id):

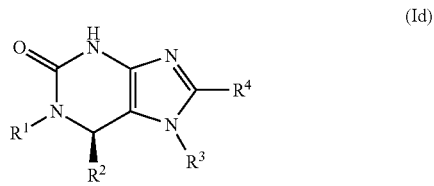

(Id)

E28 A compound according to E1 selected from:
Example 1: 1-(3-Chloro-2-fluorophenyl)-6-(4-chlorophenyl)-7-isopropyl-8-(2-methoxyphenyl)-6,7-dihydro-1H-purin-2(3H)-one;
Example 2: 1-(3-Chloro-2-fluorophenyl)-6-(4-chloro-2-methylphenyl)-7-isopropyl-8-(2-methoxyphenyl)-6,7-dihydro-1H-purin-2(3H)-one;
Example 3: 6-(4-Chloro-2-methylphenyl)-1-(5-chloro-2-methylphenyl)-7-isopropyl-8-(2-methoxyphenyl)-6,7-dihydro-1H-purin-2(3H)-one;
Example 4: 6-(4-Chloro-2-methylphenyl)-1-(5-chloro-2-methylphenyl)-7-isopropyl-8-(4-methoxypyridin-3-yl)-6,7-dihydro-1H-purin-2(3H)-one;
Example 5: 8-Bromo-1-(3-chloro-2-fluorophenyl)-6-(4-chlorophenyl)-7-isopropyl-6,7-dihydro-1H-purin-2(3H)-one;
Example 6: 1-(3-Chloro-2-fluorophenyl)-6-(4-chlorophenyl)-7-isopropyl-8-(4-methoxypyridin-3-yl)-6,7-dihydro-1H-purin-2(3H)-one;
Example 7: 6-(4-Chloro-2-methylphenyl)-1-(5-chloro-2-methylphenyl)-8-(5-fluoro-2-methoxyphenyl)-7-isopropyl-6,7-dihydro-1H-purin-2(3H)-one;
Example 8: 3-(6-(4-Chloro-2-methylphenyl)-1-(5-chloro-2-methylphenyl)-7-isopropyl-2-oxo-2,3,6,7-tetrahydro-1H-purin-8-yl)-N-(2-hydroxyethyl)-4-methoxybenzamide;
Example 9: 3-(6-(4-Chloro-2-methylphenyl)-1-(5-chloro-2-methylphenyl)-7-isopropyl-2-oxo-2,3,6,7-tetrahydro-1H-purin-8-yl)-4-methoxy-N-methylbenzamide;
Example 10: 3-(6-(4-Chloro-2-methylphenyl)-1-(5-chloro-2-methylphenyl)-7-isopropyl-2-oxo-2,3,6,7-tetrahydro-1H-purin-8-yl)-4-methoxy-N,N-dimethylbenzamide;
Example 11: 6-(4-Chloro-2-methylphenyl)-1-(5-chloro-2-methylphenyl)-8-(5-(hydroxymethyl)-2-methoxyphenyl)-7-isopropyl-6,7-dihydro-1H-purin-2(3H)-one;
Example 12: 3-(6-(4-Chloro-2-methylphenyl)-1-(5-chloro-2-methylphenyl)-7-isopropyl-2-oxo-2,3,6,7-tetrahydro-1H-purin-8-yl)-4-methoxybenzonitrile;
Example 13: 4-(1-(5-Chloro-2-methylphenyl)-7-isopropyl-8-(2-methoxyphenyl)-2-oxo-2,3,6,7-tetrahydro-1H-purin-6-yl)benzonitrile; and
Example 14: 4-(1-(3-Chloro-2-fluorophenyl)-7-isopropyl-8-(2-methoxyphenyl)-2-oxo-2,3,6,7-tetrahydro-1H-purin-6-yl)benzonitrile;
Example 15: 6-(4-Chloro-3-fluorophenyl)-1-(3-chloro-4-fluorophenyl)-8-(2,4-dimethoxypyrimidin-5-yl)-7-isopropyl-6,7-dihydro-1H-purin-2(3H)-one;
Example 16: 1-(5-Chloro-1-methyl-6-oxo-1,6-dihydropyridin-3-yl)-6-(4-chloro-2-methylphenyl)-8-(2,4-dimethoxypyrimidin-5-yl)-7-isopropyl-6,7-dihydro-1H-purin-2(3H)-one;
Example 17: 1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;
Example 18: 1-(5-Chloro-1-methyl-2-oxo-1,2-dihydropyridin-3-yl)-6-(4-chlorophenyl)-8-(2,4-dimethoxypyrimidin-5-yl)-7-isopropyl-6,7-dihydro-1H-purin-2(3H)-one;
Example 19: 1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;
Example 20: 1-(5-Chloro-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one;
Example 21: 8-(2-Amino-4-methoxypyrimidin-5-yl)-1-(5-chloro-1-methyl-2-oxo-1,2-dihydropyridin-3-yl)-6-(4-chlorophenyl)-7-isopropyl-6,7-dihydro-1H-purin-2(3H)-one;
Example 22: 1-(5-Chloro-1-methyl-2-oxo-1,2-dihydropyridin-3-yl)-6-(4-chlorophenyl)-8-(2-(dimethylamino)-4-methoxypyrimidin-5-yl)-7-isopropyl-6,7-dihydro-1H-purin-2(3H)-one;
Example 23: 6-(4-Chloro-3-fluorophenyl)-1-(3-chloro-4-fluorophenyl)-8-(2-(dimethylamino)-4-methoxypyrimidin-5-yl)-7-isopropyl-6,7-dihydro-1H-purin-2(3H)-one;
Example 24: 1-(5-Chloro-1-methyl-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one; and
Example 25: 1-(5-Chloro-2-oxo-1,2-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;
or a salt thereof.
E29 A compound according to either of E1 or E28 selected from:
Example 9: 3-(6-(4-Chloro-2-methylphenyl)-1-(5-chloro-2-methylphenyl)-7-isopropyl-2-oxo-2,3,6,7-tetrahydro-1H-purin-8-yl)-4-methoxy-N-methylbenzamide;
Example 10: 3-(6-(4-Chloro-2-methylphenyl)-1-(5-chloro-2-methylphenyl)-7-isopropyl-2-oxo-2,3,6,7-tetrahydro-1H-purin-8-yl)-4-methoxy-N,N-dimethylbenzamide;
Example 16: 1-(5-Chloro-1-methyl-6-oxo-1,6-dihydropyridin-3-yl)-6-(4-chloro-2-methylphenyl)-8-(2,4-dimethoxypyrimidin-5-yl)-7-isopropyl-6,7-dihydro-1H-purin-2(3H)-one;
Example 17: 1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;
Example 18: 1-(5-Chloro-1-methyl-2-oxo-1,2-dihydropyridin-3-yl)-6-(4-chlorophenyl)-8-(2,4-dimethoxypyrimidin-5-yl)-7-isopropyl-6,7-dihydro-1H-purin-2(3H)-one;

Example 19: 1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;

Example 20: 1-(5-Chloro-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one;

Example 22: 1-(5-Chloro-1-methyl-2-oxo-1,2-dihydropyridin-3-yl)-6-(4-chlorophenyl)-8-(2-(dimethylamino)-4-methoxypyrimidin-5-yl)-7-isopropyl-6,7-dihydro-1H-purin-2(3H)-one;

Example 24: 1-(5-Chloro-1-methyl-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one; and Example 25: 1-(5-Chloro-2-oxo-1,2-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;

or a salt thereof.

E30 A compound according to E1, E28 or E29 selected from:

Example 17: 1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;

Example 18: 1-(5-Chloro-1-methyl-2-oxo-1,2-dihydropyridin-3-yl)-6-(4-chlorophenyl)-8-(2,4-dimethoxypyrimidin-5-yl)-7-isopropyl-6,7-dihydro-1H-purin-2(3H)-one;

Example 22: 1-(5-Chloro-1-methyl-2-oxo-1,2-dihydropyridin-3-yl)-6-(4-chlorophenyl)-8-(2-(dimethylamino)-4-methoxypyrimidin-5-yl)-7-isopropyl-6,7-dihydro-1H-purin-2(3H)-one;

Example 24: 1-(5-Chloro-1-methyl-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one; and Example 25: 1-(5-Chloro-2-oxo-1,2-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;

or a salt thereof.

For purposes of interpreting this specification, terms used in the singular will also include the plural and vice versa.

In the above definitions, halo means fluoro, chloro or bromo, particularly fluoro or chloro. Alkyl, and alkoxy groups, containing the requisite number of carbon atoms, can be unbranched or branched. Examples of alkyl include, but are not limited to, methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Specific preferred compounds according to the invention are those listed in the Examples section below.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}C^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

p53 refers to the human protein itself as described by Matlashewski et al. in EMBO J. 3, 3257-62 (1984) or related family members (e.g. p73 as described in Kaghad et al. in Cell 90, 809-19 (1997) and p63 as described in Yang et al in Mol Cell 2, 305-16 (1998)) (named also p53 wild type herein) or to any variant thereof (e.g. a splice variant, mutant, fragment or isoform due to deletion, insertion and/or exchange of one or more, e.g. one to 200, of the amino acids) that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof. Where not mentioned otherwise, p53 generally relates to TP53, p53, TP73, p73, TP63, TP73L, p63, or variants thereof, respectively, as just defined. As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof. MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Research Park, Madison Wis., USA, which uses the algorithm of Smith and Waterman (Adv. Appl. Math. 2: 482-489 (1981), especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression. Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor inducing agent, an oncogene.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by MDM2 and/or MDM4, or (ii) associated with MDM2 and/or MDM4 activity, or (iii) characterized by activity (normal or abnormal) of MDM2 and/or MDM4, or (2) reducing or inhibiting the activity of MDM2 and/or MDM4, or (3) reducing or inhibiting the expression of MDM2 and/or MDM4. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of MDM2 and/or MDM4; or at least partially reducing or inhibiting the expression of MDM2 and/or MDM4.

In a further embodiment, the compounds of formula (I) are particularly useful for the treatment of disorders of diseases associated with the activity of MDM2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In another embodiment, the invention provides a pharmaceutical composition comprising a therapeutically effective amount of a compound of formula (I) or salt thereof as defined herein, and one or more pharmaceutically acceptable carriers.

The activity of a compound according to the present invention can be assessed by the following in vitro & in vivo methods.

The compounds of formula I in free form or in salt form exhibit valuable pharmacological properties, e.g. MDM2 and/or MDM4 modulating properties, e.g. as indicated in tests as provided in the next sections, and are therefore indicated for therapy.

Having regard to their inhibitory effect on p53/MDM2 and/or p53/MDM4 interaction, compounds of the formula (I) in free or pharmaceutically acceptable salt form, are useful in the treatment of conditions which are mediated by the activity (including normal activity or especially overactivity) of MDM2 and/or MDM4, or variants thereof, respectively, as described, such as proliferative and/or inflammatory conditions, e.g. by activation of the P53/MDM2 interaction, and/or that are responsive (meaning especially in a therapeutically beneficial way) to inhibition of the p53/MDM2 interaction, most especially a disease or disorder as mentioned hereinbelow.

Compounds of the invention are believed to be useful in the treatment of a disease based on dysregulation of cell cycle, such as a proliferative disorder or disease, for example cancer or tumour diseases. In particular, such diseases or disorders include benign or malignant tumors, a soft tissue sarcoma or a sarcoma such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, meningioma, glioma, mesothelioma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia such as acute myeloid leukemia or B-cell chronic lymphocytic leukemia, a lymphoma, such as of B- or T-cell origin, and metastases in other organs), viral infections (e.g. herpes, papilloma, HIV, Kaposi's, viral hepatitis).

Compounds of the invention are also believed to be useful in the treatment of or a disorder or disease involving the immune system, in particular autoimmune diseases or immune diseases resulting due to transplantation (such as rheumatoid arthritis, graft-versus-host disease, systemic lupus erythematosus, Sjögren's syndrome, multiple sclerosis, Hashimoto's thyreoiditis, polymyositis), chronic inflammatory conditions, such as asthma, osteoarthritis, atherosclerosis, Morbus Crohn or inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, pemphigus, epidermolysis bullosa acquisita, or other inflammatory or allergic conditions of the skin or hyperproliferative disorders, (e.g. Li-Fraumeni syndrome).

In another embodiment there is provided a compound of the formula (I) or salt thereof as defined herein, for use as a pharmaceutical.

A further embodiment provides a compound of the formula (I) or salt thereof as defined herein, for use in the treatment of a disorder or a disease mediated by the activity of MDM2 and/or MDM4.

A still further embodiment provides the use of a compound of formula (I) or salt thereof as defined herein, for the manufacture of a medicament for the treatment of a disorder or a disease in a subject mediated by the activity of MDM2 and/or MDM4.

As a further embodiment, the present invention provides the use of a compound of formula (I) in therapy. In a further embodiment, the therapy is selected from a disease which may be treated by inhibition of the MDM2/p53 and/or MDM4/p53 interaction, in particular the diseases or disorders listed herein.

In another embodiment, the invention provides a method of treating a disease or disorder which is treated by inhibition of the MDM2/p53 and/or MDM4/p53 interaction, comprising administration of a therapeutically acceptable amount of a compound of formula (I) or salt thereof, in particular a method of treating the diseases or disorders listed herein.

A further embodiment provides a method of modulating MDM2 and/or MDM4 activity in a subject, comprising the step of administering to a subject a therapeutically effective amount of a compound of formula (I) or salt thereof as defined herein.

The compounds of the formula (I) have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side.

The invention also relates to the use of a compound of the formula (I) (or a pharmaceutical formulation comprising a compound of the formula (I)) in the treatment of one or more of the diseases mentioned above and below where the disease(s) respond or responds (in a beneficial way, e.g. by partial or complete removal of one or more of its symptoms up to complete cure or remission) to an inhibition of the MDM2/p53 and/or MDM4/p53 interaction, especially where the involved MDM2 or MDM4 and/or variant shows (e.g. in the context of other regulatory mechanisms, due to overexpression, to mutation or the like) inadequately high or more higher than normal activity.

The invention can also relate to the use of a compound of the formula (I) to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the induction of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agents or treatments, such as side effects resulting in mucositis, stomatitis, xerostomia, gastrointestinal disorders and/or alopecia.

A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxygeldanamycin, NSC707545), IPI-504, CNF1010, CNF2024, CNF1010 from Conforma Therapeutics and AUY922; temozolomide (TEMODAL™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. under TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cisplatin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825);

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of PI3K, such as BEZ235 or BKM120;

n) compounds targeting, decreasing or inhibiting the activity of the cyclin dependent kinase family, such as PD 0332991.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1,erbitux, bevacizumab (Avastin™), rituximab (Rituxan™), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the formula (I) can be used in combination with standard leukemia therapies, especially in combination with therapies used for the treatment of AML. In particular, compounds of the formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The above-mentioned compounds, which can be used in combination with a compound of the formula (I), can be prepared and administered as described in the art, such as in the documents cited above.

A compound of the formula (I) can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of the formula (I) can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

In another embodiment, the invention provides a compound of the formula (I) or salt thereof as defined herein, in combination with one or more therapeutically active agents.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by inhibition of the MDM2/p53 and/or MDM4/p53 interaction. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by inhibition of the MDM2/p53 and/or MDM4/p53 interaction, wherein the medicament is prepared for administration with another therapeutic agent. The invention also provides the use of another therapeutic agent for treating a disease or condition mediated by inhibition of the MDM2/p53 and/or MDM4/p53 interaction, wherein the medicament is administered with a compound of formula (I).

The invention also provides a compound of formula (I) for use in a method of treating a disease or condition mediated by inhibition of the MDM2/p53 and/or MDM4/p53 interaction, wherein the compound of formula (I) is prepared for administration with another therapeutic agent. The invention also provides another therapeutic agent for use in a method of treating a disease or condition mediated by inhibition of the MDM2/p53 and/or MDM4/p53 interaction, wherein the other therapeutic agent is prepared for administration with a compound of formula (I). The invention also provides a compound of formula (I) for use in a method of treating a disease or condition mediated by inhibition of the MDM2/p53 and/or MDM4/p53 interaction, wherein the compound of formula (I) is administered with another therapeutic agent. The invention also provides another therapeutic agent for use in a method of treating a disease or condition mediated by inhibition of the MDM2/p53 and/or MDM4/p53 interaction, wherein the other therapeutic agent is administered with a compound of formula (I).

The invention also provides the use of a compound of formula (I) for treating a disease or condition mediated by inhibition of the MDM2/p53 and/or MDM4/p53 interaction, wherein the patient has previously (e.g. within 24 hours) been treated with another therapeutic agent. The invention also provides the use of another therapeutic agent for treating a disease or condition mediated by inhibition of the MDM2/p53 and/or MDM4/p53 interaction, wherein the patient has previously (e.g. within 24 hours) been treated with a compound of formula (I).

Typically, the compounds of formula (I) can be prepared according to the Schemes provided infra.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

ABBREVIATIONS

Ac acetyl
AcOH acetic acid
$AlCl_3$ aluminium trichloride
ACN acetonitrile
aq. aqueous
API atmospheric pressure ionization
Boc tert-butoxycarbonyl
brine saturated (at rt) sodium chloride solution
bs broad singlet
$^n$BuOH n-butanol
$^t$Bu tert-butyl
CDI carbonyl diimidazole
Celite trademark of Celite Corp. (World Minerals Inc.), Santa Barbara, Calif., USA, for filtering aid based on kieselguhr
$CH_3CN$ acetonitrile
conc. concentrated
d doublet
DCM dichloromethane
DEA diethylamine
DIEA N,N-diethyl-isopropylamine
DMAP 4-dimethylaminopyridine
DME 1,2-Dimethoxyethane
DMF N,N-dimethylformamide
DMSO dimethylsulfoxide
DPPA diphenylphosphoryl azide
ES-MS electrospray mass spectrometry
Et ethyl
$Et_3N$ triethylamine
$Et_2O$ diethyl ether
EtOAc ethyl acetate
EtOH ethanol
equiv equivalents
h hour(s)
HATU O-(7-azabenzotriazol-1-yl)-N,N,N',N'-tetramethyluronium-hexafluorophosphate
HBr hydrogen bromide
HCl hydrogen chloride
HOAt 1-hydroxy-7-azabenzotriazole
HPLC high-performance liquid chromatography
IPAm isopropylamine
iPr isopropyl
$K_2CO_3$ potassium carbonate
KHMDS potassium hexamethyldisilazide
KOAc potassium acetate
KO$^t$Bu potassium-tert-butoxylate
KOH potassium hydroxide
$K_3PO_4$ potassium phosphate
LAH lithium aluminium hydride
LC liquid chromatography
LDA lithium diisopropylamide
LiOH lithium hydroxide
Me methyl
MeI methyl iodide
MeOH methanol
$MgSO_4$ magnesium sulphate
m multiplet
min minute(s)
mL milliliter(s)
MS Mass Spectrometry
MsCl methanesulfonyl chloride
$Ms_2O$ methanesulfonic anhydride
NaH sodium hydride
$NaHCO_3$ sodium bicarbonate
$Na_2CO_3$ sodium carbonate
$NaNO_2$ sodium nitrite
NaOH sodium hydroxide
NaOMe sodium methoxide
NaOEt sodium ethoxide
NaO$^t$Bu sodium tert-butoxide
$Na_2SO_4$ sodium sulphate
NBS N-bromosuccinimide
NCS N-chlorosuccinimide
n.d. not determined
$NH_4Cl$ ammonium chloride
$NH_4OH$ ammonium hydroxide
NIS N-iodosuccinimide
NMM 4-N-methylmorpholine
NMR nuclear magnetic resonance
Ph phenyl
$POCl_3$ Phosphoryl chloride
rt (or RT) room temperature
$R_f$ TLC retention factor
s singulet
$scCO_2$ super critical $CO_2$
sep septet
$SnCl_2$ Stannous chloride
t triplet
TBAF tetrabutylammonium fluoride
TBAHS tetrabutylammonium hydrogen sulphate
TBME tert-butylmethylether
TBTU O-(benzotriazol-1-yl)-N,N,N',N'-tetramethylammonium tetrafluoroborate
TEA triethylamine
TFA trifluoroacetic acid
TFAA trifluoroacetic anhydride
THF tetrahydrofurane
TLC thin layer chromatography
TMS trimethylsilyl
TMSCl trimethylsilyl chloride
$t_R$ time of retention TsCl p-toluenesulfonyl chloride
TsOH p-toluenesulfonic acid
UV ultraviolet General Methods.

1H-NMR measurements were performed on a Bruker Ultrashield™ 400 (400 MHz), Bruker Ultrashield™ 600 (600 MHz) or a 500 MHz DRX Bruker CryoProbe (500 MHz) spectrometer using or not trimethylsilane as an internal standard. Chemical shifts (d-values) are reported in ppm downfield from tetramethylsilane, coupling constants (J) are given in Hz, spectra splitting pattern are designated as singlet (s), doublet (d), doublet doublet (dd), triplet (t), quadruplet (q), quintuplet (quin), multiplet or more overlapping signals (m), broad signal (br). Solvents are given in parentheses.

TLC were performed with precoated silica gel 60 $F_{254}$ glass plates (Merck, Darmstadt, Germany) using the respective named solvent systems. Visualization was generally done by UV light (254 nm).

HPLC/LC-MS Methods:

HPLC 1:
  Column: Chromolith RP18 3×100 mm.
  Flow: 1.3 ml/min.
  Gradient: 2% to 100% B in 6 min;
  Solvent A=0.1% TFA in water,
  Solvent B=0.1% TFA in acetonitrile HPLC 2:
  System: LaChrom Elite
  Detection: 215 nm
  Column: Chromolit RP-18e 100–3 mm, 5 mu
  Flow: 1.5 ml/min
  Gradient: 2-100% ACN en 3 min, 100% 2 min (3-5 min), 100-2% in 0.1 min (5-5.1 min) et 2% ACN de 5.1-6 min HPLC 3:
  System: HP 1100
  Detection: 215 nm
  Column: Nucleosil 100-3 C18 HD 4.0×125 mm
  Solvent A: water+0.1% TFA
  Solvent B: Acetonitril+0.1% TFA
  Flow: 1.0 ml/min
  Gradient: 0 to 7 min: 2% to 100% B, 7 to 9 min: 100% B, 9 to 10 min: 100 to 2% B HPLC 4:
  System: Waters
  Detection PDA 210-300
  Column: Nucleosil 100-3 C18 HD 4.0×125 mm
  Solvent A: water+0.1% TFA
  Solvent B: Acetonitril+0.1% TFA
  Flow: 1.0 ml/min
  Run time: 15 min
  Gradient: 0 to 7 min: 2% to 100% B, 7 to 9 min: 100% B, 9 to 10 min: 100 to 2% B HPLC 5:
  System: Waters
  Column: Acquity UPLC BEH C18, 2.1*50 mm, 1.7 um
  Solvent A: water+0.1% TFA
  Solvent B: Acetonitril+0.1% TFA
  Flow: 0.6 ml/min
  Run time: 6.5 min
  Gradient: 0.5 min 5% B, 5-100% B in 3.5 min, 1.5 min 100% B, 100-5% B in 1 min.

LC-MS 1:
  Column: Acquity HSS T3 2.1×50 mm, 1.8 μm.
  Flow: 1.2 ml/min. Column temperature: 50° C.
  Gradient: 2% to 98% B in 1.4 min, 98% B for 0.75 min, 98% to 2% B in 0.04 min, 2% B for 0.01 min;
  Solvent A=water+0.05% formic acid+3.75 mM ammonium acetate,
  Solvent B=acetonitrile+0.04% formic acid
  Detection full scan: 215-350 nM LC-MS 2:
  Column: Acquity HSS T3 2.1×50 mm, 1.8 μm.
  Flow: 1.2 ml/min.
  Column temperature: 50° C.
  Gradient: 2% to 98% B in 1.4 min, 98% B for 0.75 min, 98% to 2% B in 0.04 min, 2% B for 0.01 min;
  Solvent A=water+0.05% formic acid+0.05% ammonium acetate,
  Solvent B=acetonitrile+0.04% formic acid
  Detection full scan: 215-350 nM LC-MS 3:
  Column: Ascentis Express C18 2.1×30 mm, 2.7 μm.
  Flow: 1.2 ml/min.
  Column temperature: 50° C.
  Gradient: 2% to 98% B in 1.4 min, 98% B for 0.75 min, 98% to 2% B in 0.04 min, 98% B for 0.01 min;
  Solvent A=water+0.05% formic acid+0.05% ammonium acetate,
  Solvent B=acetonitrile+0.04% formic acid LC_MS 4:
  System: Waters Acquity UPLC with Waters SQ detector
  Column: Acquity HSS T3 1.8 μm 2.1×50 mm at 50° C.
  Flow rate: 1.2 ml/min
  Eluent A: H2O+0.05% formic acid+3.75 mM ammonium acetate
  Eluent B: acetonitrile+0.04% formic acid
  Gradient: from 2 to 98% B in 1.4 min, 98% B for 0.75 min, 98% to 2% B in 0.04 min, 98% B for 0.01 min;

MS methods:

MS 1: Electrospray ionization mass spectra. Positive and negative alternating.
  Detection: DAD-UV 210-400 nm. Scan range 100-1600 Da in 0.4 seconds Preparative HPLC Methods Preparative HPLC Method 1: Sf 30×100 50-90%:
  System: Gilson system with Pumps 331 and 332, UV detector/Vis-155 and liquid Handler GX-281
  Column: Waters sunfireC18, 5 um, 30×100 mm with guard column 19×10 mm
  Solvent A: Water+0.1% TFA
  Solvent B: Acetonitrile
  Flow: 50 ml/min Preparative Standard:
  System: Gilson system with Pumps 331 and 332, UV detector/Vis-155 and liquid Handler GX-281
  Column: sunfire prep C18, 5 um, 30×100 mm with guard column 19×10 mm
  Solvent A: Water+0.1% TFA
  Solvent B: Acetonitrile
  Flow: 30 ml/min
  Gradient: 5-100% B in 20 min.

In the following generic schemes, R substituents are referred to as follows and are as defined as in Formula (I):

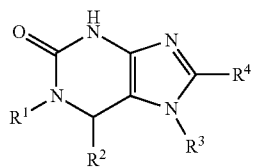

Scheme 1

Scheme 1 illustrates one method of preparing compounds of the invention (e.g. example 1).

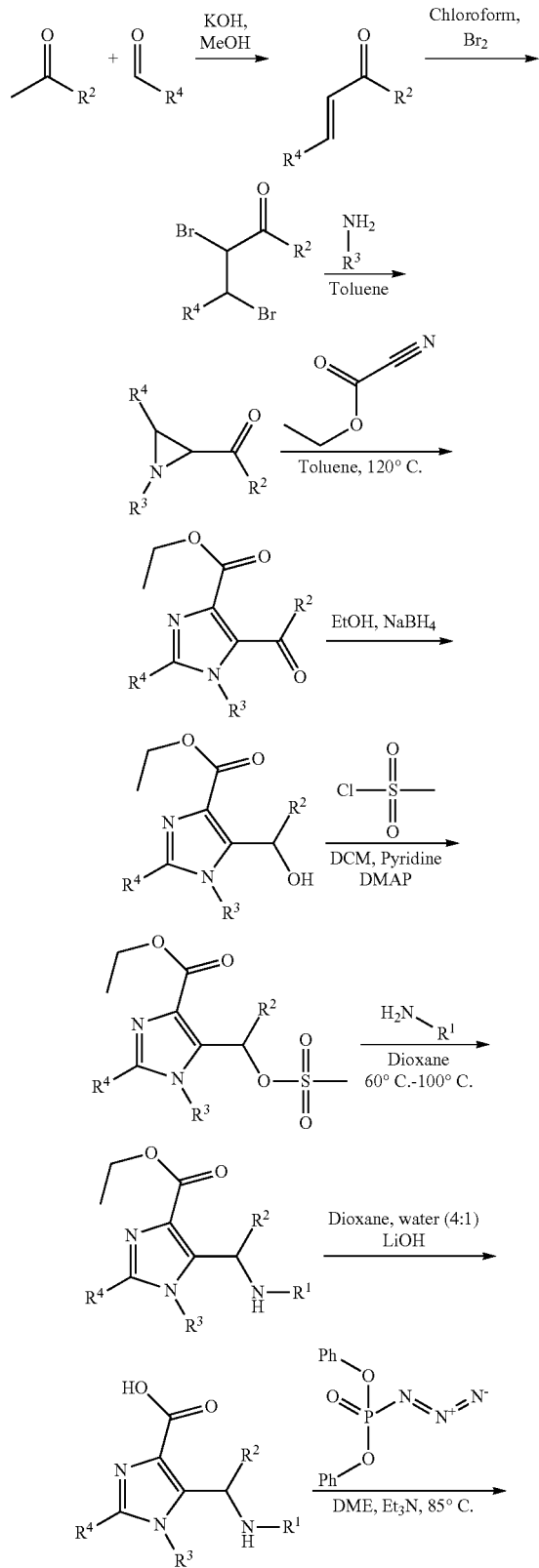

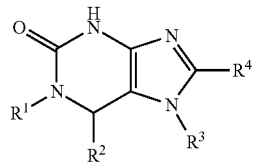

The condensation of a representative ketone and aldehyde was carried out in methanol at room temperature in the presence of a base such as potassium hydroxide. The product was brominated at room temperature in a solvent such as chloroform. A representative amine was added to a solution of the product of the bromination step in a solvent such as toluene with cooling. Ethyl carbonocyanidate was added to a solution of the product of the previous step in a solvent such as toluene at elevated temperature. The product was reduced with $NaBH_4$ in a solvent such as ethanol at room temperature. Methanesulfonyl chloride was added together with pyridine in a solvent such as DCM. DMAP was added to the reaction mixture and stirred at room temperature. A representative amine was added to a solution of the product of the previous step in a solvent such as dioxane and stirred at elevated temperature. LiOH was added to a solution of the product of the previous step a solvent such as dioxane and $H_2O$. The mixture was stirred at elevated temperature. DPPA and $Et_3N$ was added to a solution of the product of the previous step in a solvent such as 1,2-dimethoxyethane and was stirred at elevated temperature.

Scheme 2

Scheme 2 illustrates one method of preparing compounds of the invention (e.g. examples 2 and 3)

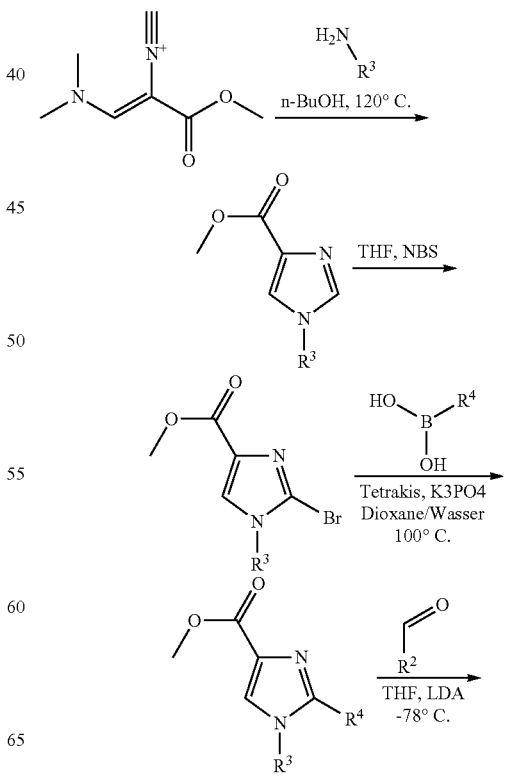

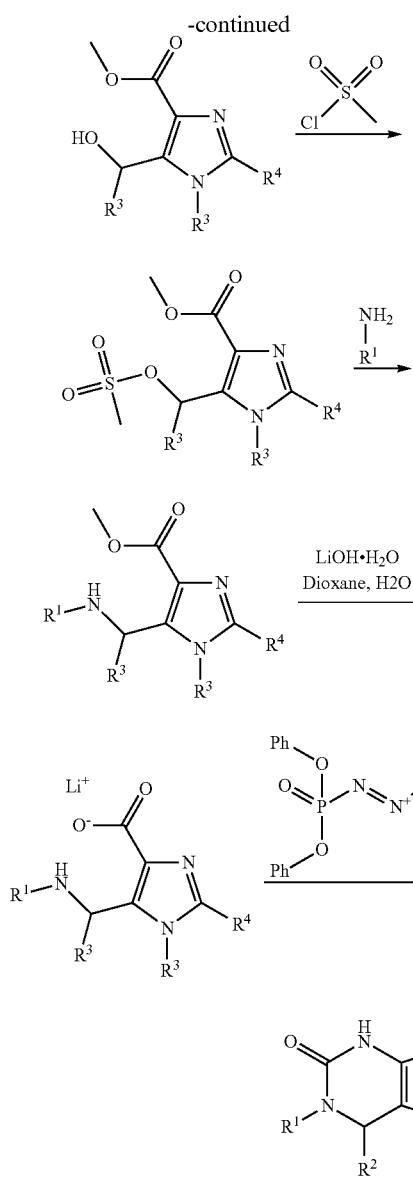

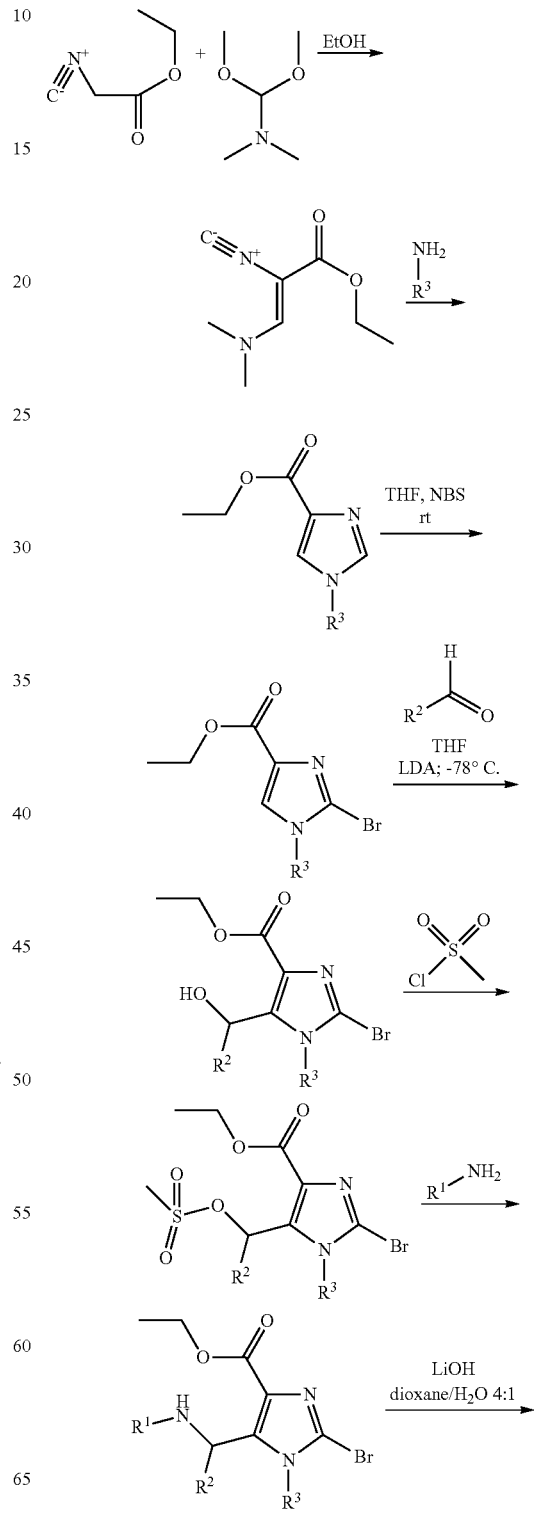

An appropriate amine was reacted with (Z)-1-(dimethylamino)-3-methoxy-N-methylidyne-3-oxoprop-1-en-2-aminium in a suitable solvent such as butanol at elevated temperature. NBS was added to a solution of the product of the first step in a suitable solvent such as THF at RT. A solution of the product of the previous step, $K_3PO_4$, an appropriate boronic acid, and $Pd(PPh_3)_4$ in a solvent such as dioxane/$H_2O$ was stirred under argon in a sealed tube at elevated temperature. A solution of the product of the previous step in a solvent such as THF was cooled down to around −78° C. under argon. LDA was added to the reaction mixture and stirred at around −78° C. A solution of an appropriate aldehyde in a solvent such as THF was added and stirred at around −78° C. The mixture was allowed to warm and quenched with, for example, AcOH. Methanesulfonyl chloride was added to a solution of the product of the previous step and TEA in a solvent such as DCM at RT. An appropriate amine was added to a solution of the product of the previous step in a solvent such as DCM at RT. $LiOH.H_2O$ was added to a solution of the product of the previous step in a solvent such as a mixture of dioxane/water and stirred at elevated temperature. To a solution of the product of the previous step and $Et_3N$ in a solvent such as DME, DPPA was added and the mixture was stirred at elevated temperature.

Scheme 3

Scheme 3 illustrates one method of preparing compounds of the invention (e.g. examples 4 to 25)

-continued

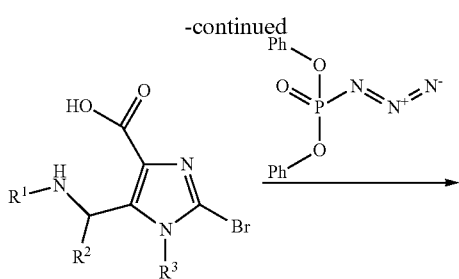

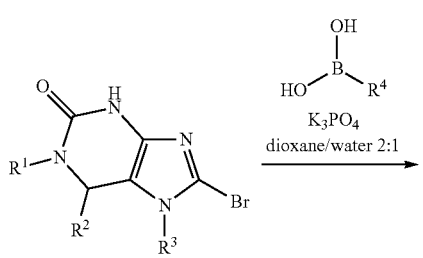

A solution of ethyl-2-isocyanoacetate in a solvent such as ethanol was cooled and 1,1-dimethoxy-N,N-dimethyl methanamine was added and the reaction mixture allowed to reach RT. An appropriate amine was added to a solution of the product of the first step in a suitable solvent such as n-BuOH and the reaction stirred at elevated temperature. NBS was added to a solution of the product of the previous step in a solvent such as THF and the mixture was stirred under argon. A solution of the product of the previous step in a solvent such as THF was cooled to around −78° C. and LDA solution was added and the solution stirred at around −78° C. A solution of a suitable aldehyde in a solvent such as THF was added dropwise to the mixture and stirred at around −73° C. To a solution of the product of the previous step in a solvent such as DCM, TEA and methanesulfonyl chloride were added and stirred at RT. To a solution of the product of the previous step in a solvent such as DCM, an appropriate amine was added and stirred at RT. To a solution of the product of the previous step in a solvent such as dioxane and water, LiOH.H$_2$O was added and stirred at RT. To a solution of the product of the previous step in 1,2-dimethoxyethane, TEA and DPPA were added and stirred at elevated temperature. To a solution of the product of the previous step in a solvent such as dioxane and water, an appropriate boronic acid, tetrakis(triphenylphosphine)palladium(0) and tripotassium phosphate were added and stirred at an elevated temperature.

Example 1

1-(3-Chloro-2-fluoro-phenyl)-6-(4-chloro-phenyl)-7-isopropyl-8-(2-methoxy-phenyl)-1,3,6,7-tetrahydro-purin-2-one

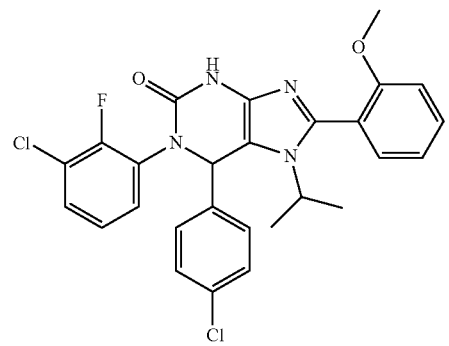 [SMILES: COc1ccccc1-c1nc2c(n1C(C)C)C(c1ccc(Cl)cc1)N(c1cccc(Cl)c1F)C(=O)N2]

DPPA (0.034 ml, 0.156 mmol) and Et$_3$N (0.022 ml, 0.156 mmol) was added to a solution of the product of step 1.1 (55 mg, 0.104 mmol) in 1,2-dimethoxyethane (1 ml) and was stirred at 85° C. for 2 hours. The solution was diluted with EtOAc and washed with 5% aqueous citric acid solution, saturated aqueous NaHCO$_3$ solution and brine. The water phase was back extracted with EtOAc. The combined organic layers were dried over Na$_2$SO$_4$ and evaporated to give 53 mg brown solid, which was purified by preparative HPLC (Column xBridge (30/100 mm), 30 ml/min, 0.1% TFA-water/0.1% TFA-acetonitrile; gradient acetonitrile 5 to 40% in 4 min, then 40 to 90% in 15 min and 3 min at 100%) to afford 19 mg (0.034 mmol, 33% yield) of the title compound. LCMS: (M+H)=524/526; t$_R$=1.20 min (LC-MS 3). 1H-NMR (d$_6$-DMSO, 600.13 MHz) δ ppm 7.50 (m, 1H) 7.43 (t, 1H) 7.34 (d, 2H) 7.30 (m, 1H) 7.20-7.04 (m, 6H) 6.09 (s, 1H) 4.05 (q, 1H) 3.64 (s, 3H) 1.23 (d, 3H) 0.80 (bs., 3H).

Step 1.1: 5-((3-Chloro-2-fluorophenylamino)(4-chlorophenyl)methyl)-1-isopropyl-2-(2-methoxyphenyl)-1H-imidazole-4-carboxylic acid

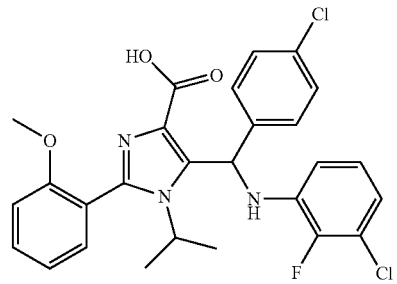 [SMILES: COc1ccccc1-c1nc(C(=O)O)c(C(Nc2cccc(Cl)c2F)c2ccc(Cl)cc2)n1C(C)C]

LiOH.H$_2$O (16.97 mg, 0.404 mmol) was added to a solution of the product of step 1.2 (150 mg, 0.270 mmol) in dioxane (2 ml) and H$_2$O (0.5 ml). The mixture was stirred at 60° C. for 3 hours. The reaction mixture was diluted with EtOAc and washed twice with a 5% aqueous citric acid solution. The water phase was back extracted with EtOAc. The organic layers were combined and washed with brine, dried over Na$_2$SO$_4$ and evaporated to give 155 mg (0.264 mmol, 98% yield) of the title compound as a yellow solid, which was used in the next step without purification. LCMS: (M+H)=528/529; $t_R$=1.19 min (LC-MS 3). HPLC: $t_R$=4.86 min (HPLC 2). 1H-NMR (CD3OD, 400 MHz) δ ppm 7.60 (bs, 1H) 7.41 (bs, 1H) 7.39 (s, 4H) 7.18-7.10 (m, 2H) 6.98-6.75 (m, 4H) 4.71 (m, 1H) 3.79 (s, 3H) 1.27 (d, 3H) 1.11 (bs, 3H)

Step 1.2: Ethyl-5-((3-chloro-2-fluorophenylamino)(4-chlorophenyl)methyl)-1-isopropyl-2-(2-methoxyphenyl)-1H-imidazole-4-carboxylate

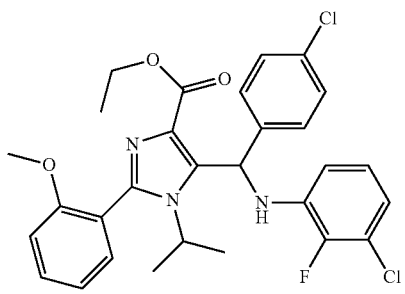 [SMILES: CCOC(=O)c1nc(-c2ccccc2OC)n(C(C)C)c1C(Nc1cccc(Cl)c1F)c1ccc(Cl)cc1]

3-chloro-2-fluoroaniline (90 mg, 0.621 mmol) was added to a solution of the product of step 1.3 (242 mg, 0.477 mmol) in dioxane (5 ml) and stirred at 60° C. over night. 3-Chloro-2-fluoroaniline (90 mg, 0.621 mmol) was added again to the reaction mixture and heated at 100° C. for 3 hr. The solution was diluted with EtOAc and washed twice with a 5% aqueous citric acid solution. The water phase was back extracted with EtOAc and the combined organic layers were washed with saturated aqueous NaHCO₃, dried over Na₂SO₄ and evaporated to afford 800 mg of brown oil. The residue was purified by preparative HPLC (Waters xBridge (30/100 mm), 0.1% TFA-water/0.1% TFA-acetonitrile; gradient acetonitrile 30 to 60% in 10 min, then 5 min at 60%, 60-90% in 10 min and 2 min at 100%) to afford 176 mg (0.313 mmol, 65.6% yield) of the title compound. LCMS: (M+H)=556/557; $t_R$=1.46 min (LC-MS 3). HPLC: $t_R$=5.35 min (HPLC 2) 1H-NMR (MeOD, 600.13 MHz) δ ppm 7.52 (t, 1H) 7.39-7.30 (m, 5H) 7.12 (m, 1H) 7.07 (t, 1H) 6.96 (t, 1H) 6.86 (t, 1H) 6.77 (t, 1H) 6.72-6.30 (m, 1H) 4.37 (quin, 1H) 4.27 (q, 2H) 3.77 (s, 3H) 1.31-1.05 (m, 9H)

Step 1.3: Ethyl-5-((4-chlorophenyl)(methylsulfonyloxy)methyl)-1-isopropyl-2-(2-methoxyphenyl)-1H-imidazole-4-carboxylate

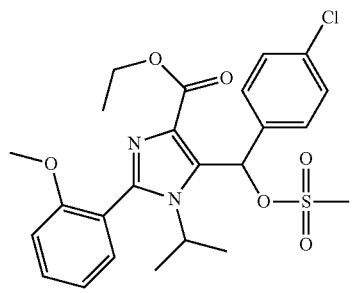

Methanesulfonyl chloride (82 mg, 0.717 mmol) was added to a solution of the product of step 1.4 (205 mg, 0.478 mmol) and pyridine (0.077 ml, 0.956 mmol) in DCM (5 ml). DMAP (17.52 mg, 0.143 mmol) was added to the reaction mixture and stirred at RT for 15 hr. Pyridine (0.077 ml, 0.956 mmol) and methanesulfonyl chloride (82 mg, 0.717 mmol) were added again. Later more pyridine (0.077 ml, 0.956 mmol) and methanesulfonyl chloride (82 mg, 0.717 mmol) were added and the solution was stirred at reflux temperature (40° C.) for 2 hr. The mixture was diluted with DCM and saturated aqueous NH₄Cl, washed twice with saturated aqueous NH₄Cl. The water phase was back extracted, and the organic layer phase was dried over Na₂SO₄ and evaporated to afford 550 mg of the title compound as a dark brown oil, which was use in the next step without purification.

Step 1.4: Ethyl-5-((4-chlorophenyl)(hydroxy)methyl)-1-isopropyl-2-(2-methoxyphenyl)-1H-imidazole-4-carboxylate

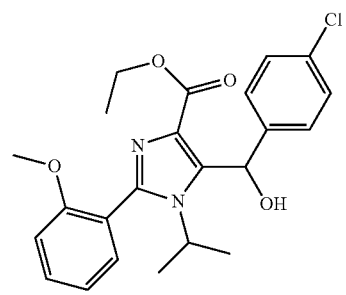 [SMILES: CCOC(=O)c1nc(-c2ccccc2OC)n(C(C)C)c1C(O)c1ccc(Cl)cc1]

28.7 mg (0.759 mmol) NaBH₄ was added to a solution of the product of step 1.5 (216 mg, 0.506 mmol) in EtOH (5 ml). The solution was stirred at RT for 48 hours. After that the mixture was quenched with H₂O, diluted with EtOAc and washed twice with a 5% aq. citric acid solution. The water phase was back extracted with EtOAc and the combined organic phases were washed with saturated NaHCO₃, dried over Na₂SO₄ and evaporated to afford 210 mg (0.465 mmol, 92% yield) of the title compound as a yellow solid. LCMS: (M+H)=429; $t_R$=1.16 min (LC-MS 3). 1H-NMR (MeOD, 400 MHz) δ ppm 7.50 (t, 1H) 7.36 (s, 4H) 7.34-7.32 (m, 1H) 7.09-6.99 (m, 3H) 4.70 (m, 1H) 4.32 (q, 2H) 3.76 (s, 3H) 1.34 (t, 3H) 1.20-1.12 (m, 3H) 0.70 (d, 3H)

Step 1.5: Ethyl-5-(4-chlorobenzoyl)-1-isopropyl-2-(2-methoxyphenyl)-1H-imidazole-4-carboxylate

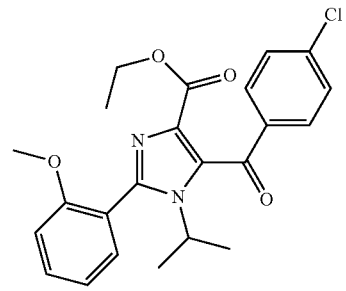 [SMILES: CCOC(=O)c1nc(-c2ccccc2OC)n(C(C)C)c1C(=O)c1ccc(Cl)cc1]

1.486 ml (15.16 mmol) ethyl carbonocyanidate was added to a solution of the product of step 1.6 (5 g, 15.16 mmol) in toluene (100 ml) and stirred at 110° C. for 5 hours. The reaction mixture was cooled down, diluted with EtOAc and water and washed twice with water. The water phase was back extracted and the combined organic layers were evaporated to give 910 mg brown oil, which was purified by chromatography (Silicagel, 100% Heptane to 80% EtOAc-20% Heptane) to afford 547 mg (1.269 mmol, 8.37% yield) of the title compound. LCMS: (M+H)=427; $t_R$=1.23 min (LC-MS 3). 1H-NMR ($d_6$-DMSO, 400 MHz) δ ppm 7.86 (d, 2H) 7.67 (d, 2H) 7.56 (t, 1H) 7.46 (d, 1H) 7.22 (d, 1H) 7.11 (t, 1H) 4.15 (quin, 1H) 3.93 (q, 2H) 3.81 (s, 3H) 1.20 (d, 6H) 0.88 (t, 3H)

Step 1.6: (4-Chlorophenyl)(1-isopropyl-3-(2-methoxyphenyl)aziridin-2-yl)methanone

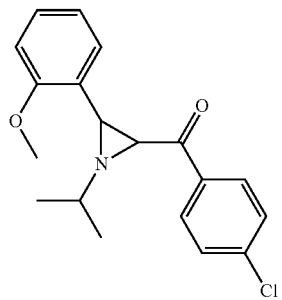 [SMILES: COc1ccccc1C1C(C(=O)c2ccc(Cl)cc2)N1C(C)C]

5.49 ml (64.5 mmol) propan-2-amine was added to a solution of the product of step 1.7 (9.3 g, 21.50 mmol) in toluene (100 ml) at 0° C. The reaction mixture was stirred for 24 hours and slowly warmed up to RT (white precipitate formed). The precipitate was separated by filtration and the solvent was evaporated to give 7.9 g brown oil, which was purified by chromatography (Silicagel, 100% Heptane to EtOAc/Heptane 1:1) to afford 6.9 g (20.92 mmol, 97% yield) of the title compound. LCMS: (M+H)=330; $t_R$=1.23 min (LC-MS 3). 1H-NMR ($d_6$-DMSO, 400 MHz) δ ppm 7.89 (d, 2H) 7.53 (d, 2H) 7.26 (d, 1H) 7.09 (t, 1H) 6.78 (m, 2H) 3.61 (m, 4H) 3.30 (m, 1H) 2.03 (quin, 1H) 1.14 (d, 6H).

Step 1.7: 2,3-Dibromo-1-(4-chlorophenyl)-3-(2-methoxyphenyl)propan-1-one

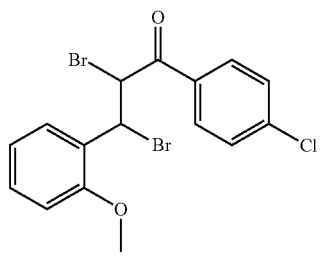 [SMILES: COc1ccccc1C(Br)C(Br)C(=O)c1ccc(Cl)cc1]

1.266 ml (24.57 mmol) $Br_2$ was slowly added to a solution of the product of step 1.8 (6.7 g, 24.57 mmol) in chloroform (200 ml) at 65° C. The solution was stirred for 20 min. The reaction mixture was cooled down and diluted with $CH_2Cl_2$. The organic layer was washed twice with $Na_2S_2O_3$ (3% w/w aqueous solution). The water phase was back extracted with $CH_2Cl_2$ and the combined organic layers were dried over $Na_2SO_4$ and evaporated to give 10.36 g (23.71 mmol, 97% yield) of the title compound as a yellow resin. 1H-NMR ($d_6$-DMSO, 600.13 MHz) Mixture of isomers δ ppm 8.28 (d, 1H) 8.05 (d, 1H) 7.71 (d, 1H) 7.60 (d, 1H) 7.53-7.37 (m, 1H) 7.21 (t, 1H) 7.08-6.93 (m, 1H) 6.83 (t, 1H) 6.70 (d, 1H) 6.10-5.87 (d, 1H) 3.90-3.79 (s, 3H).

Step 1.8: (E)-1-(4-chlorophenyl)-3-(2-methoxyphenyl)prop-2-en-1-one

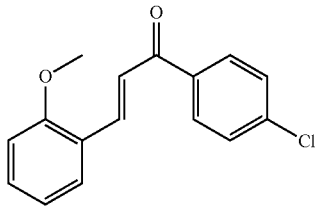 [SMILES: COc1ccccc1/C=C/C(=O)c1ccc(Cl)cc1]

KOH (1.415 g, 25.2 mmol) was added to a solution of 1-(4-chlorophenyl)ethanone (3.9 g, 25.2 mmol) and 2-methoxybenzaldehyde (3.43 g, 25.2 mmol) in methanol (100 ml) at RT and the solution was stirred for 18 hours. The solution was concentrated under reduced pressure until a precipitate was formed. AcOH (1.444 ml, 25.2 mmol) was added and the mixture was cooled down to 0° C.-5° C. The mixture was stirred for 1 hour and the light yellow precipitate was separated by filtration and washed with cold methanol to afford 6.72 g (24.39 mmol, 97% yield) of the title compound. LCMS: (M+H)=273; $t_R$=1.28 min (LC-MS 3). 1H-NMR ($d_6$-DMSO, 600 MHz) δ ppm 8.12 (d, 2H) 8.04 (d, 1H) 7.98 (d, 1H) 7.86 (d, 1H) 7.62 (d, 2H) 7.45 (t, 1H) 7.10 (d, 1H) 7.02 (t, 1H) 3.88 (s, 3H).

Example 2

1-(3-Chloro-2-fluoro-phenyl)-6-(4-chloro-2-methyl-phenyl)-7-isopropyl-8-(2-methoxy-phenyl)-1,3,6,7-tetrahydro-purin-2-one

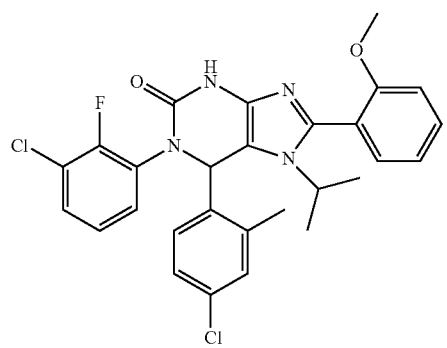 [SMILES: COc1ccccc1-c1nc2c(n1C(C)C)C(c1ccc(Cl)cc1C)N(c1cccc(Cl)c1F)C(=O)N2]

To a solution of the product of step 2.1 (150 mg, 0.22 mmol) and $Et_3N$ (46 μl, 0.33 mmol) in DME (2 ml), DPPA (71 μl, 0.33 mmol) was added and the mixture was stirred at 85° C. for 5 hours. The reaction mixture was diluted with EtOAc and extracted with a 5% citric acid solution. The organic layer was washed with a saturated $NaHCO_3$ solution, dried ($Na_2SO_4$), filtered and concentrated. The crude material was purified by flash chromatography ($CH_2Cl_2$/MeOH, 100:0→94:6) to afford 95 mg (0.167 mmol, 76% yield) of the title compound. LCMS: (M+H)=539/541; $t_R$=1.25 min (LC-MS 1). $^1$H-NMR ($d_6$-DMSO, 400 MHz) δ ppm 9.95 (s, 1H)

7.85 (m, 1H) 7.56-7.03 (m, 9H) 5.50 (d, 1H) 4.12 (m, 1H) 3.75 (s, 3H) 1.74 (s, 3H) 1.16-0.55 (m, 6H)

Step 2.1: 5-[(3-Chloro-2-fluoro-phenylamino)-(4-chloro-2-methyl-phenyl)-methyl]-1-isopropyl-2-(2-methoxy-phenyl)-1H-imidazole-4-carboxylate

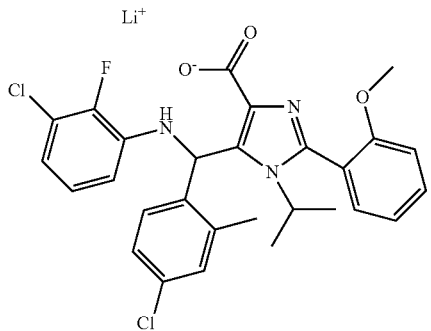 [SMILES: [Li+] ; COc1ccccc1-c1nc(C(=O)[O-])c(C(Nc2cccc(Cl)c2F)c2ccc(Cl)cc2C)n1C(C)C]

LiOH.H₂O (31.7 mg, 0.755 mmol) was added to a solution of the product of step 2.2 (280 mg, 0.503 mmol) in a mixture of 5 ml dioxane/water (4:1) and stirred at 60° C. for 3 hours. The solvent was evaporated and the residue was dried on high vacuum at 60° C. for 18 hours to afford 340 mg (0.496 mmol, 99% yield) of the title compound as a lithium salt. LCMS: (M+H)=542/544; $t_R$=1.27 min (LC-MS 4). HPLC: $t_R$=2.77 min (HPLC 2). ¹H-NMR (d₆-DMSO, 400 MHz) δ ppm 7.47 (t, 1H) 7.32 (m, 1H) 7.28 (d, 1H) 7.16 (m, 1H) 7.11 (d, 1H) 7.04-6.94 (m, 5H) 6.75-6.66 (m, 1H) 4.64 (bs, 1H) 3.69 (s, 3H) 2.41 (s, 3H) 1.348-0.81 (m, 6H).

Step 2.2: 5-[(3-Chloro-2-fluoro-phenylamino)-(4-chloro-2-methyl-phenyl)-methyl]-1-isopropyl-2-(2-methoxy-phenyl)-1H-imidazole-4-carboxylic acid methyl ester

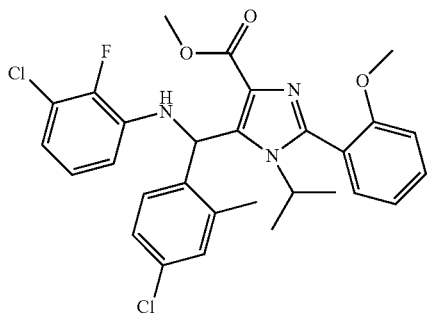 [SMILES: COC(=O)c1nc(-c2ccccc2OC)n(C(C)C)c1C(Nc1cccc(Cl)c1F)c1ccc(Cl)cc1C]

3-chloro-2-fluoroaniline (310 mg, 2.130 mmol) was added to a solution of the product of step 2.3 (800 mg, 0.710 mmol) in DCM (10 ml) at RT and the solution was stirred for 16 hours. The solvent was evaporated and the crude reaction mixture was taken up in EtOAc (ca. 10 ml) and Et₃N (500 µl) and stirred for 5 min. The white precipitate was filtered and the clear yellow solution containing the product was purified by chromatography (Silicagel, heptane, heptane-EtOAc 1:1) to afford 290 mg (0.469 mmol, 66.1% yield) of the title compound. LCMS: (M+H)=556/558; $t_R$=1.42 min (LC-MS 1). HPLC: $t_R$=5.17 min (HPLC 2). ¹H-NMR (d₆-DMSO, 400 MHz) δ ppm 7.49 (t, 1H) 7.39-7.20 (m, 4H) 7.10 (d, 1H) 7.00 (m, 3H) 6.76 (t, 2H) 6.66 (bs, 1H) 4.64 (bs, 1H) 3.69-3.61 (m, 6H) 2.27 (s, 3H) 1.08-0.81 (m, 6H)

Step 2.3: Methyl-5-((4-chloro-2-methylphenyl)(methylsulfonyloxy)methyl)-1-isopropyl-2-(2-methoxyphenyl)-1H-imidazole-4-carboxylate

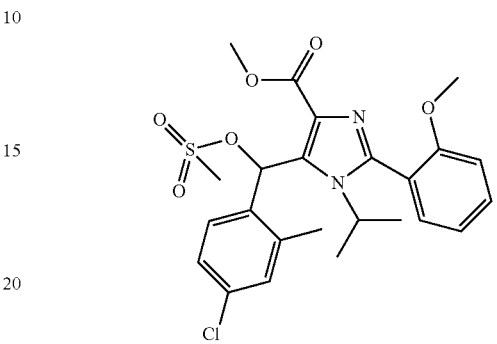

Methanesulfonyl chloride (0.225 ml, 2.89 mmol) was added to a solution of the product of step 2.4 (620 mg, 1.446 mmol) and TEA (0.504 ml, 3.61 mmol) in DCM (15 ml) at RT and stirred for 6 hours. The solvent was evaporated to afford 1.6 g (1.420 mmol, 98% yield) of the title compound, which was used in the next step without purification.

Step 2.4: 5-[(4-Chloro-2-methyl-phenyl)-hydroxy-methyl]-1-isopropyl-2-(2-methoxy-phenyl)-1H-imidazole-4-carboxylic acid methyl ester

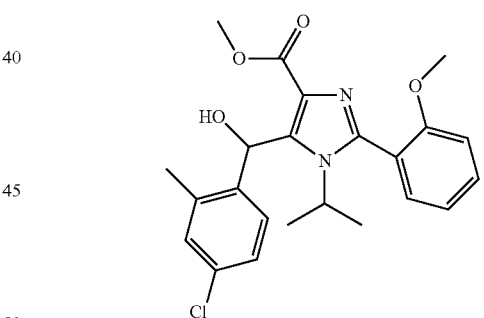

A solution of the product of step 2.5 (450 mg, 1.640 mmol) in 15 ml THF was cooled down to −78° C. under argon. LDA (2.73 ml, 4.92 mmol) was slowly added to the reaction mixture and stirred at −78° C. for 1.5 h. A solution of 4-chloro-2-methylbenzaldehyde (761 mg, 4.92 mmol) in 3 ml THF was slowly added and stirred for 1 hour at −78° C. Then reaction mixture was slowly warmed up and quenched with AcOH at −30° C. Then the mixture was diluted with EtOAc and washed with saturated aqueous NaHCO₃ and brine. The water phase was back extracted with EtOAc. The combined organic phases were evaporated and purified by chromatography (silicagel, heptane, heptane-EtOAc 7:3) to afford 580 mg (1.285 mmol, 78% yield) of the title compound. LCMS: (M+H)=429; $t_R$=1.17 min (LC-MS 1). HPLC: $t_R$=4.28 min (HPLC 2).

Step 2.5: 1-Isopropyl-2-(2-methoxy-phenyl)-1H-imidazole-4-carboxylic acid methyl ester

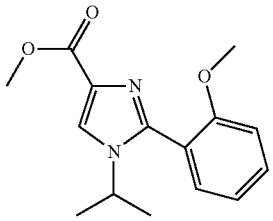 [SMILES: COC(=O)c1cn(C(C)C)c(-c2ccccc2OC)n1]

A solution of the product of step 2.6 (1.75 g, 7.08 mmol), K$_3$PO$_4$ (3.76 g, 17.71 mmol), 2-methoxyphenylboronic acid (1.29 g, 8.50 mmol) and Pd(PPh$_3$)$_4$ (818 mg, 0.71 mmol) in dioxane/H$_2$O (50 ml, 4:1) was stirred under argon in a sealed tube at 100° C. for 3 hours. The reaction mixture was purified by preparative MPLC (Waters xbridge C18, 0.1% TFA-water/ 0.1% TFA-acetonitrile; gradient acetonitrile 5 to 60% in 20 min) to afford 1.54 g (5.05 mmol, 71.3% yield) of the title compound. LCMS: (M+H)=275; $t_R$=0.74 min (LC-MS 1). HPLC: $t_R$=2.17 min (HPLC 2). 1H-NMR (d$_6$-DMSO, 400 MHz) δ ppm 7.62-7.47 (m, 2H) 7.30 (dd, 1H) 7.15 (d, 1H) 7.05 (t, 1H) 3.97 (m, 1H) 3.75 (s, 3H) 3.73 (s, 3H) 1.29 (d, 6H)

Step 2.6: 2-Bromo-1-isopropyl-1H-imidazole-4-carboxylic acid methyl ester

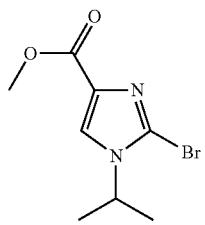

NBS (6.05 g, 34.0 mmol) was added to a solution of the product of step 2.7 (6.5 g, 30.9 mmol) in THF (120 ml) at RT. The solution was stirred over night. 3 g NBS were added again and the reaction mixture was stirred for 4 hours. The mixture was diluted with EtOAc and washed twice with Na$_2$S$_2$O$_3$ (3% aq.) and brine. The water phase was back extracted with EtOAc and the combined organic phases were evaporated and purified by chromatography (silicagel, heptane, heptane-EtOAc 1:1) to afford 1.77 g (6.81 mmol, 22.01% yield) of the title compound. LCMS: (M+H)=248/250; $t_R$=0.66 min (LC-MS 1). R$_f$=0.51 (EtOAc/hexane 1:1). HPLC: $t_R$=3.19 min (HPLC 2). 1H-NMR (d$_6$-DMSO, 400 MHz) δ ppm 8.20 (s, 1H) 4.41 (quin, 1H) 3.73 (s, 3H) 1.39 (d, 6H)

Step 2.7: 1-Isopropyl-1H-imidazole-4-carboxylic acid methyl ester

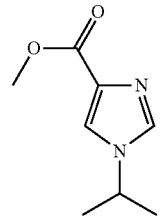

Propan-2-amine (27.4 ml, 322 mmol) was added to a solution of (Z)-1-(dimethylamino)-3-methoxy-N-methylidyne-3-oxoprop-1-en-2-aminium (5 g, 32.2 mmol) in n-BuOH (50 ml). The flask was sealed and heated to 120° C. for 5 hr. The solvent was evaporated. The crude was taken up in EtOAc and washed with water and brine. The water phase was back extracted with EtOAc. The combined organic phase was dried over Na$_2$SO$_4$ and evaporated to afford 6.5 g (30.9 mmol, 96% yield) of the title compound as a black oil. LCMS: (M+H)=169; $t_R$=0.34 min (LC-MS 1). 1H-NMR (d$_6$-DMSO, 400 MHz) δ ppm 8.00 (d, 1H) 7.82 (d, 1H) 4.44 (quin, 1H) 3.71 (s, 3H) 1.39 (d, 6H)

Example 3

6-(4-Chloro-2-methylphenyl)-1-(5-chloro-2-methylphenyl)-7-isopropyl-8-(2-methoxyphenyl)-6,7-dihydro-1H-purin-2(3H)-one

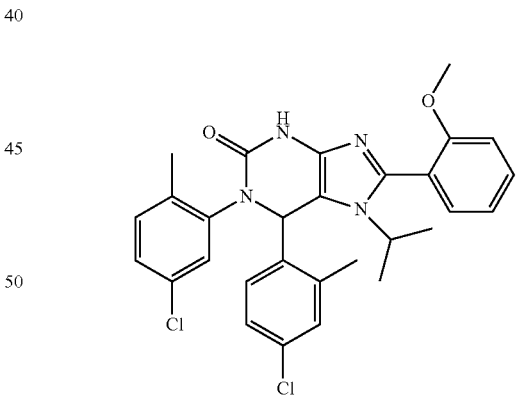

Example 3 was obtained following the synthesis of example 2, however 5-chloro-2-methylaniline (302 mg, 2.130 mmol) was used in step 2.2 instead of 3-chloro-2-fluoroaniline. LCMS: (M+H)=535/537; $t_R$=1.29 min (LC-MS 1). HPLC: $t_R$=2.74 min (Method HPLC 2). 1H-NMR (d$_6$-DMSO, 400.13 MHz, 100° C.) isomers mixture, δ ppm 7.73, 6.41 (s, 1H) 7.47 (m, 1H) 7.39-7.03 (m, 9H) 6.07, 5.94 (s, 1H) 3.93 (dt, 1H) 3.76 (s, 3H) 1.78-1.28 (m, 6H) 1.12 (m, 3H) 0.66 (m, 3H).

Example 4

6-(4-Chloro-2-methylphenyl)-1-(5-chloro-2-methylphenyl)-7-isopropyl-8-(4-methoxypyridin-3-yl)-6,7-dihydro-1H-purin-2(3H)-one

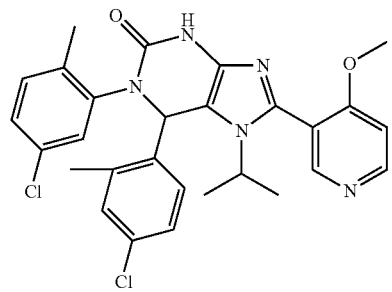 [SMILES: COc1ccncc1-c1nc2c(n1C(C)C)C(c1ccc(Cl)cc1C)N(c1cc(Cl)ccc1C)C(=O)N2]

To a solution of the product of step 4.1 (40 mg, 0.079 mmol) in 0.525 ml dioxane and 0.262 ml water, 24 mg (0.157 mmol) 2-methoxy-5-pyridineboronic acid, 19 mg (18.19 mmol) tetrakis(triphenylphosphine)palladium(0) and 67 mg tripotassium phosphate were added and stirred at 100° C. for 3 hours. The reaction mixture was diluted in EtOAc and water. The water phase was extracted with EtOAc and the combined organic phases were washed with dried $Na_2SO_4$, filtered and evaporated. The residue was purified by chromatography (Silicagel, 100% hexane to 100% EtOAc in 25 minutes) to give 21 mg oil, which was purified again by preparative HPLC (Prep. HPLC Method 1, gradient 50-90% B in 16 minutes). The pure fractions were joined and EtOAc was added. The mixture was washed with $NaHCO_3$, dried ($Na_2SO_4$), filtered and evaporated to afford 18 mg (0.032 mmol, 40.5% yield) of the title compound as a pale yellow foam. LCMS: (M+H)=536/538; $t_R$=1.23 min (LC-MS 4). 1H-NMR ($d_6$-DMSO, 600.13 MHz) δ ppm 9.60, 9.45 (s, 1H) 8.29 (m, 1H) 7.80 (m, 1H) 7.71, 6.07 (s, 1H) 7.39-7.09 (m, 5H) 6.92 (d, 1H) 6.42, 5.95 (s, 1H) 4.29-4.09 (m, 1H) 3.95 (s, 3H) 2.32-1.44 (m, 6H) 1.21 (m, 3H) 0.78 (m, 3H)

Step 4.1: 8-Bromo-6-(4-chloro-2-methylphenyl)-1-(5-chloro-2-methylphenyl)-7-isopropyl-6,7-dihydro-1H-purin-2(3H)-one

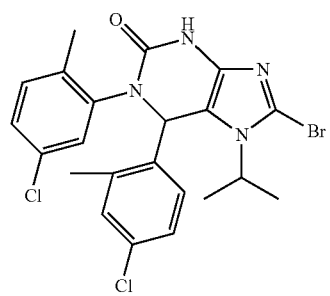 [SMILES: Cc1cc(Cl)ccc1C1c2c(nc(Br)n2C(C)C)NC(=O)N1c1cc(Cl)ccc1C]

To a solution of the product of step 4.2 (200 mg, 0.391 mmol) in 3.9 ml 1,2-dimethoxyethane, 82 μl (0.587 mmol) TEA and 126 μl (0.587 mmol) DPPA were added and stirred at 85° C. for 2 hours. The reaction mixture was partitioned between water/$NaHCO_3$, and extracted twice with EtOAc. The combined organic phases were washed with brine, dried with $Na_2SO_4$ and evaporated. The residue was purified by chromatography (Silicagel, 100% DCM to DCM/MeOH 9:1 in 18 minutes) to give 88 mg (0.164 mmol, 42.0% yield) of the title compound as a yellow solid. LCMS: (M+H)=509; $t_R$=1.23 min (LC-MS 4); 1H-NMR ($d_6$-DMSO, 600.13 MHz) Isomers mixture δ ppm 9.65, 9.52 (m, 1H) 7.71, 6.04 (s, 1H) 7.37-7.04 (m, 5H) 6.41, 5.69 (s, 1H) 4.16-4.00 (m, 1H) 2.29, 1.44 (s, 3H) 1.78 (s, 3H) 1.11 (m, 6H).

Step 4.2: 2-Bromo-5-((4-chloro-2-methylphenyl)(5-chloro-2-methylphenylamino)methyl)-1-isopropyl-1H-imidazole-4-carboxylic acid

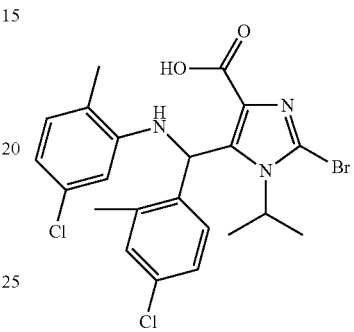

To a solution of the product of step 4.3 (1.18 g, 1.969 mmol) in 16 ml dioxane and 4 ml water, 124 mg (2.95 mmol) $LiOH \cdot H_2O$ were added and stirred at RT for 16 hours. 62 mg $LiOH \cdot H_2O$ were added again and the solution was stirred at RT for 24 hours. EtOAc was added to the solution and the mixture was washed with a 5% citric acid solution, dried over $Na_2SO_4$, filtered and evaporated to give 1.2 g (1.878 mmol, 95% yield) of the title compound as a yellow foam. LCMS: (M+H)=512; $t_R$=1.29 min (LC-MS 4); 1H-NMR ($d_6$-DMSO, 400 MHz) δ ppm 12.88 (bs., 1H) 7.38 (m, 1H) 7.26 (m, 1H) 7.03 (d, 1H) 6.95 (d, 1H) 6.79 (bs, 1H) 6.61 (m, 1H) 6.44 (bs, 1H) 6.00 (bs, 1H) 5.04 (m, 1H) 2.24 (s, 3H) 2.11 (s, 3H) 1.43 (d, 3H) 1.33 (d, 3H).

Step 4.3: Ethyl-2-bromo-5-((4-chloro-2-methylphenyl)(5-chloro-2-methylphenylamino)methyl)-1-isopropyl-1H-imidazole-4-carboxylate

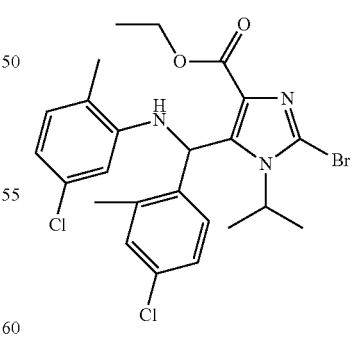

To a solution of the product of 4.4 (3.1 g, 3.77 mmol) in 10 ml DCM, 1.4 ml (11.30 mmol) 5-chlor-2-methylaniline was added and stirred at RT for 3 hours. Later at 4° C., 1.4 ml 5-chlor-2-methylaniline was added again and the solution was stirred at RT for 16 hours. The reaction mixture was partitioned between water and DCM, and washed with water, dried over Na₂SO₄ and evaporated. The residue was purified by chromatography (Silicagel, 100% Hexane to 20% EtOAc in 22 min) to give 1.8 g yellow oil, which was re-crystallised in hexane to afford 1.18 g (1.969 mmol, 52.3% yield) of the title compound as a pale yellow solid. LCMS: (M+H)=540; $t_R$=1.46 min (LC-MS 4); 1H-NMR (d₆-DMSO, 400 MHz) δ ppm 7.39 (d, 1H) 7.26 (m, 1H) 7.03 (d, 1H) 6.98 (d, 1H) 6.77 (bs, 1H) 6.61 (m, 1H) 6.37 (bs, 1H) 5.96 (d, 1H) 5.05 (m, 1H) 4.24 (m, 2H) 2.21 (s, 3H) 2.12 (s, 3H) 1.41 (d, 3H) 1.33 (d, 3H) 1.25 (t, 3H)

Step 4.4: Ethyl-2-bromo-5-((4-chloro-2-methylphenyl)(methylsulfonyloxy)methyl)-1-isopropyl-1H-imidazole-4-carboxylate

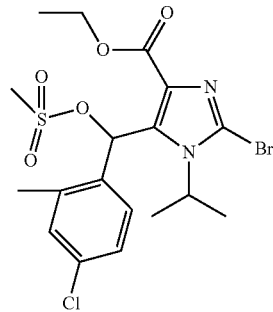 [SMILES: CCOC(=O)c1nc(Br)n(C(C)C)c1C(OS(C)(=O)=O)c1ccc(Cl)cc1C]

To a solution of the product of step 4.5 (1.57 g, 3.878 mmol) in 38 ml DCM, 1.3 ml (9.44 mmol) TEA and 0.589 ml (7.55 mmol) methanesulfonyl chloride were added and stirred at RT for 16 hours. The reaction mixture was concentrated and dried on high vacuum to give 3.1 g (3.77 mmol, 100% yield) of the title compound. LCMS: $t_R$=1.19 min (LC-MS 4); 1H-NMR (d₆-DMSO, 400 MHz) δ ppm 7.66 (d, 1H) 7.56 (s, 1H) 7.43-7.39 (m, 2H) 4.65 (quin, 1H) 4.27 (m, 2H) 2.33 (s, 3H) 2.13 (s, 3H) 1.55 (d, 3H) 1.27 (t, 3H) 1.14 (d, 3H).

Step 4.5: Ethyl-2-bromo-5-((4-chloro-2-methylphenyl)(hydroxy)methyl)-1-isopropyl-1H-imidazole-4-carboxylate

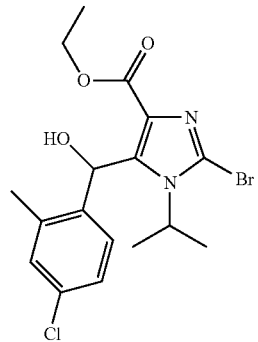 [SMILES: CCOC(=O)c1nc(Br)n(C(C)C)c1C(O)c1ccc(Cl)cc1C]

A solution of the product of step 4.6 (2.21 g, 7.62 mmol) in 70 ml THF was cooled to −78° C., and 12.7 ml (22.85 mmol) LDA solution (1.8M) was added and the solution was stirred at −78° C. for 1.5 hours. A solution of 3.53 g (22.85 mmol) 4-chloro-2-methylbenzaldehyde in 8 ml THF was added dropwise to the mixture and stirred at −73° C. for 1 hour. The mixture was partitioned between water and EtOAc. The water phase was extracted twice with EtOAc and the combined organic phases were washed with brine, dried over Na₂SO₄ and evaporated. The residue was crystallized (hexane) to afford 1.57 g (3.44 mmol, 45.1% yield) of the title compound as a beige solid. LCMS: (M+H)=415/417; $t_R$=1.18 min (LC-MS 1); 1H-NMR (d₆-DMSO, 400 MHz) δ ppm 7.47 (d, 1H) 7.32 (dd, 1H) 7.27 (d, 1H) 6.85 (d, 1H) 6.60 (d, 1H) 4.78 (quin, 1H) 4.25 (q, 2H) 2.11 (s, 3H) 1.45 (d, 3H) 1.28 (t, 3H) 1.03 (d, 3H)

Step 4.6: Ethyl 2-bromo-1-isopropyl-1H-imidazole-4-carboxylate

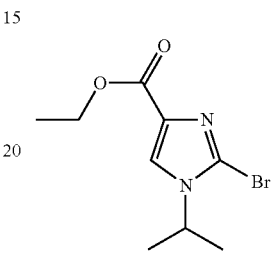

NBS (12.89 g, 72.4 mmol) was added to a solution of the product of step 4.7 (12 g, 65.9 mmol) in 200 ml THF. The reaction mixture was stirred under argon for 16 hours. After that NBS (6.5 g) was added again and the solution was stirred for 2 hours. The mixture was diluted with EtOAc (300 ml). The organic phase was washed with a 3% Na₂S₂O₃ aqueous solution and with brine. The water phase was extracted with EtOAc. The combined organic phases were evaporated and the crude product was purified by chromatography (Silicagel, heptane to heptane/EtOAc 1:4) to afford 4.16 g (15.93 mmol, 24.19% yield) of the title compound. LCMS: (M+H)=261/263; $t_R$=0.77 min (LC-MS 1); 1H-NMR (d₆-DMSO, 400 MHz) δ ppm 8.16 (s, 1H) 4.44 (m, 1H) 4.20 (q, 2H) 1.40 (d, 6H) 1.26 (t, 3H)

Step 4.7: Ethyl-1-isopropyl-1H-imidazole-4-carboxylate

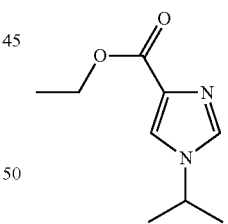

Propan-2-amine (54.4 ml, 638 mmol) was added to a solution of the product of step 4.8 (10.8 g, 63.8 mmol) in n-BuOH (80 ml) and stirred at 130° C. for 15 hours. The reaction mixture was diluted with EtOAc (300 ml) and 100 ml 1M HCl was slowly added to the mixture. The solution was diluted with 100 ml water. The phases were separated and the organic phase was washed with brine. The water phase was back extracted twice with EtOAc and the combined organic phases were evaporated to give 12.08 g (53.0 mmol, 83% yield) of the title compound as a brown oil, which was used in the next step without purification. HPLC: $t_R$=1.97 min (Method HPLC 2). 1H-NMR (d₆-DMSO, 400 MHz) δ (ppm) 7.96 (s, 1H), 7.81 (s, 1H) 4.44 (m, 1H), 4.17 (q, 2H) 1.38 (d, 6H) 1.23 (t, 3H)

Step 4.8: (Z)-3-Dimethylamino-2-isocyano acrylic acid ethyl ester

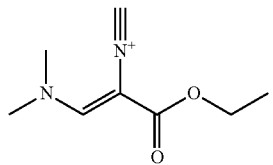

A solution of ethyl-2-isocyanoacetate (10.3 g, 91 mmol) in ethanol (100 ml) was cooled down to 0° C. 1,1-dimethoxy-N,N-dimethyl methanamine (26.6 ml, 200 mmol) was added and the reaction mixture was then allowed to reach RT and stirred for 24 h. The mixture was concentrated and the crude material was purified by flash chromatography (heptane/EtOAc, 100:0 to 40:60) to afford 11 g (64.7 mmol, 71.1% yield) of the title compound. LCMS: (M+H)=169; $t_R$=0.74 min (LC-MS 2); 1H-NMR (CDCl$_3$, 400 MHz) δ (ppm) 7.15 (s, 1H), 4.18 (q, 2H), 3.20 (bs, 6H), 1.26 (t, 3H).

The following examples were synthesized in analogy to the synthesis of example 4 using the appropriate building blocks:

Example 5

8-Bromo-1-(3-chloro-2-fluorophenyl)-6-(4-chlorophenyl)-7-isopropyl-6,7-dihydro-1H-purin-2(3H)-one

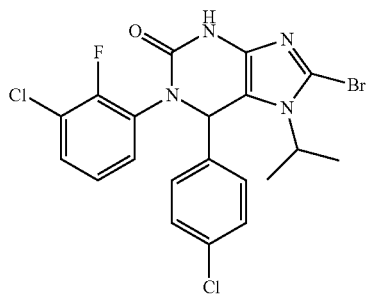 [SMILES: CC(C)n1c(Br)nc2c1C(c1ccc(Cl)cc1)N(c1cccc(Cl)c1F)C(=O)N2]

LCMS: (M+H)=497/499/501; $t_R$=1.14 min (LC-MS 4). 1H-NMR (d$_6$-DMSO, 399.97 MHz) δ ppm 10.13 (s, 1H) 7.47 (t, 1H) 7.37 (d, 2H) 7.22-7.06 (m, 4H) 6.14 (bs, 1H) 4.18 (m, 1H) 1.15 (m, 6H).

Example 6

1-(3-Chloro-2-fluorophenyl)-6-(4-chlorophenyl)-7-isopropyl-8-(4-methoxypyridin-3-yl)-6,7-dihydro-1H-purin-2(3H)-one

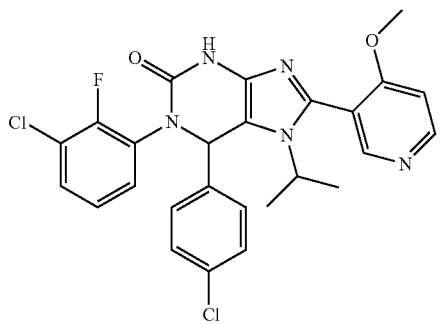 [SMILES: COc1ccncc1-c1nc2c(n1C(C)C)C(c1ccc(Cl)cc1)N(c1cccc(Cl)c1F)C(=O)N2]

LCMS: (M+H)=526/528; $t_R$=1.16 min (LC-MS 4). 1H-NMR (d$_6$-DMSO, 600.13 MHz) δ ppm 10.06 (s, 1H) 8.30 (s, 1H) 7.83 (d, 1H) 7.65-7.07 (m, 7H) 6.95 (d, 1H) 6.15 (bs, 1H) 4.27 (m, 1H) 3.91 (s, 3H) 1.25 (d, 3H) 0.72 (bs, 3H).

Example 7

1-(5-Chloro-2-methyl-phenyl)-6-(4-chloro-2-methyl-phenyl)-8-(5-fluoro-2-methoxy-phenyl)-7-isopropyl-1,3,6,7-tetrahydro-purin-2-one

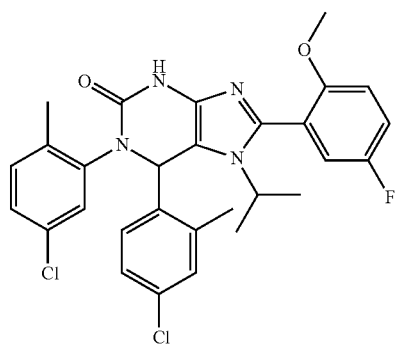 [SMILES: COc1ccc(F)cc1-c1nc2c(n1C(C)C)C(c1ccc(Cl)cc1C)N(c1cc(Cl)ccc1C)C(=O)N2]

LCMS: (M+H)=553/555; $t_R$=1.32 min (LC-MS 1). 1H-NMR (d$_6$-DMSO, 600.13 MHz, 100° C.) Rotamers δ ppm 9.53, 9.39 (s, 1H) 7.73, 6.07 (s, 1H) 7.65-6.99 (m, 8H) 6.41, 5.94 (m, 1H) 3.94 (m, 1H) 3.75 (s, 3H) 2.33-1.44 (m, 6H) 1.16-1.10 (m, 3H) 0.70-0.65 (m, 3H).

Example 8

3-[1-(5-Chloro-2-methyl-phenyl)-6-(4-chloro-2-methyl-phenyl)-7-isopropyl-2-oxo-2,3,6,7-tetrahydro-1H-purin-8-yl]-N-(2-hydroxy-ethyl)-4-methoxy-benzamide

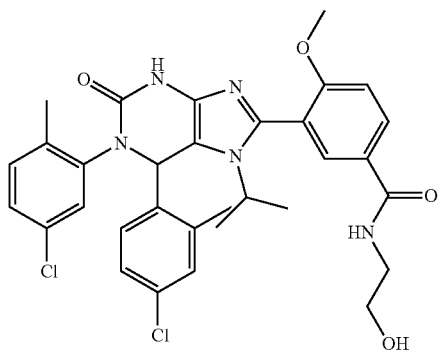 [SMILES: COc1ccc(C(=O)NCCO)cc1-c1nc2c(n1C(C)C)C(c1ccc(Cl)cc1C)N(c1cc(Cl)ccc1C)C(=O)N2]

The title compound was prepared in analogy to the procedure described for example 4 but using the product of step 8.1 and 8-bromo-6-(4-chloro-2-methylphenyl)-1-(5-chloro-2-methylphenyl)-7-isopropyl-6,7-dihydro-1H-purin-2(3H)-one (product of step 4.1). LCMS: (M+H)=622/624; $t_R$=1.08 min (LC-MS 1). 1H-NMR (d$_6$-DMSO, 600.13 MHz, 100° C.) δ ppm 9.53, 9.38 (m, 1H) 8.11 (t, 1H) 8.00 (m, 1H) 7.88 (d, 1H) 7.73, 6.08 (m, 1H) 7.67-7.18 (m, 6H) 6.43, 5.95 (m, 1H)

4.40 (bs, 1H) 3.97-3.88 (m, 1H) 3.83 (s, 3H) 3.56 (m, 2H) 3.38 (m, 2H) 2.33-1.44 (m, 6H) 1.20 (m, 3H) 0.68 (m, 3H).

Step 8.1:
5-(2-Hydroxyethylcarbamoyl)-2-methoxyphenylboronic acid

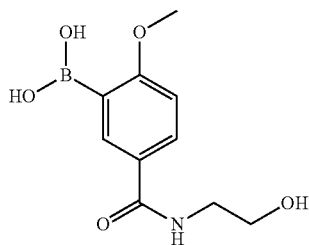 [SMILES: COc1ccc(C(=O)NCCO)cc1B(O)O]

To a solution of 800 mg (4.08 mmol) 3-bromo-4-methoxybenzoic acid in 40 ml DMF, 0.493 µl (8.16 mmol) 2-aminoethanol, 1.7 g (4.49 mmol) HATU and 1.8 ml (16.33 mmol) NMM were added and stirred at RT for 3 hours. The reaction mixture was added to EtOAc and water. The water phase was extracted 3 times with EtOAc. The combined organic phases were dried over $Na_2SO_4$, filtered and evaporated. The crude product was triturated in EtOAc and crystals were filtered. To the water phase, NaCl was added and extracted with EtOAc and THF. The combined organic phases were dried ($Na_2SO_4$) filtered and evaporated and the crystal was filtered. Combined solids afforded 469.6 mg (1.965 mmol, 48.1% yield) of the title compound as colorless crystals. LCMS: (M+H)=240; $t_R$=0.43 min (LC-MS 4). 1H-NMR ($d_6$-DMSO, 400 MHz,) δ ppm 8.04 (m, 1H) 7.95-7.85 (m, 1H) 7.79 (m, 1H) 7.06-6.98 (m, 1H) 4.68 (t, 1H) 3.82 (s, 3H) 3.48 (m, 2H) 3.29 (m, 2H).

0.1% TFA-water/acetonitrile; gradient acetonitrile 5-100% in 20 min). LCMS: (M+H)=592/594; $t_R$=1.15 min (LC-MS 1).

Step 9.1:
2-Methoxy-5-(methylcarbamoyl)phenylboronic acid

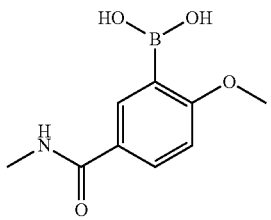

3-Borono-4-methoxybenzoic acid (2.5 g, 12.50 mmol) was dissolved in DMF (6 ml) and 12.50 ml methylamine (2 M solution in THF, 25 mmol) was added followed by HATU (4.75 mg, 12.5 mmol) and NMM (1.375, 12.50 mmol). The reaction mixture was stirred at RT for 20 hours and concentrated. The crude material was added to 50 ml water and extracted 3 times with EtOAc. The combined organic phases were dried ($Na_2SO_4$), filtered and concentrated. The crude material was triturated in EtOAc and filtered. The residue was purified by chromatography (Silicagel, $CH_2Cl_2$/MeOH 95:5) to give 1.92 g (7.11 mmol, 56.9% yield) of the title compound as a colorless solid. LCMS: (M+H)=210; $t_R$=0.50 min (LC-MS 1). TLC: $R_f$=0.27 ($CH_2Cl_2$/MeOH 95:5). HPLC: $t_R$=3.76 min (HPLC 3). 1H-NMR ($d_6$-DMSO, 600.13 MHz) δ ppm 8.29 (bs, 1H), 8.03 (s, 1H), 7.87 (d, 1H), 7.85 (s, 2H) 7.02 (d, 1H), 3.84 (s, 3H), 2.75 (d, 3H).

Example 9

3-[1-(5-Chloro-2-methyl-phenyl)-6-(4-chloro-2-methyl-phenyl)-7-isopropyl-2-oxo-2,3,6,7-tetrahydro-1H-purin-8-yl]-4-methoxy-N-methyl-benzamide

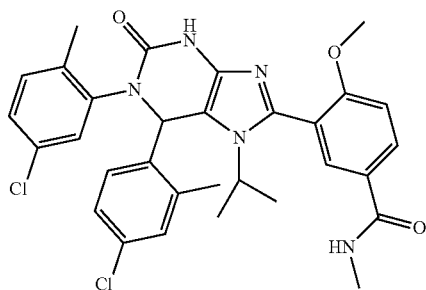 [SMILES: CNC(=O)c1ccc(OC)c(-c2nc3c(n2C(C)C)C(c2ccc(Cl)cc2C)N(c2cc(Cl)ccc2C)C(=O)N3)c1]

The title compound was prepared in analogy to the procedure described for example 4 but using the product of step 9.1 and 8-bromo-6-(4-chloro-2-methylphenyl)-1-(5-chloro-2-methylphenyl)-7-isopropyl-6,7-dihydro-1H-purin-2(3H)-one (product of step 4.1). The crude material was purified by preparative HPLC (Waters Sun Fire C18, 30×100 mm, 5 µm;

Example 10

3-[1-(5-Chloro-2-methyl-phenyl)-6-(4-chloro-2-methyl-phenyl)-7-isopropyl-2-oxo-2,3,6,7-tetrahydro-1H-purin-8-yl]-4-methoxy-N,N-dimethyl-benzamide

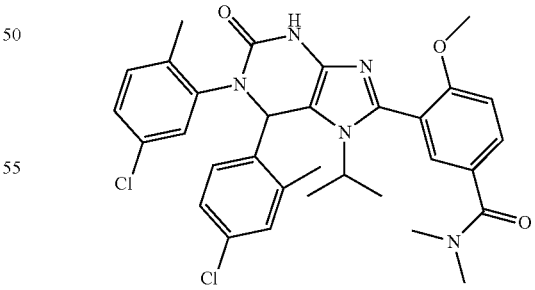

The title compound was prepared in analogy to the procedure described for example 4 but using the product of step 10.1 and 8-bromo-6-(4-chloro-2-methylphenyl)-1-(5-chloro-2-methylphenyl)-7-isopropyl-6,7-dihydro-1H-purin-2(3H)-one (product of step 4.1). LCMS: (M+H)=606/608; $t_R$=1.18 min (LC-MS 1).

Step 10.1:
5-(Dimethylcarbamoyl)-2-methoxyphenylboronic acid

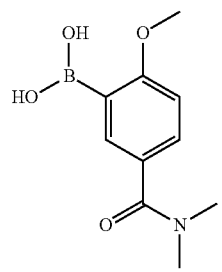 [SMILES: COc1ccc(C(=O)N(C)C)cc1B(O)O]

To a solution of 700 mg (3.57 mmol) 3-borono-4-methoxybenzoic acid in 23 ml DMF, 3.6 ml (7.14 mmol) dimethylamine, 1.5 g (3.93 mmol) HATU and 1.57 ml (14.29 mmol) NMM were added and stirred at RT for 2 hours. The reaction mixture was extracted with EtOAc and water. The organic phase was dried over Na$_2$SO$_4$, filtered and evaporated. The residue was purified by preparative HPLC (Prep. HPLC method 1, gradient: 15-30% in 16 minutes). The fractions containing product were combined and extracted twice with EtOAc. The combined organic phases were dried over Na$_2$SO$_4$, filtered and evaporated to afford 361 mg (1.619 mmol, 45.3% yield) of the title compound as a colorless solid. LCMS: (M+H)=224; t$_R$=0.54 min (LC-MS 4). 1H-NMR (d$_6$-DMSO, 400 MHz) δ ppm 7.56 (m, 1H) 7.44 (dd, 1H) 6.99 (d, 1H) 3.81 (s, 3H) 2.93 (s, 6H).

Example 11

1-(5-Chloro-2-methyl-phenyl)-6-(4-chloro-2-methyl-phenyl)-8-(5-hydroxymethyl-2-methoxy-phenyl)-7-isopropyl-1,3,6,7-tetrahydro-purin-2-one

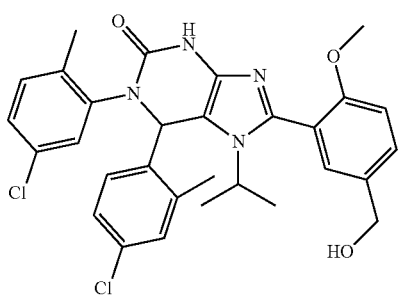 [SMILES: COc1ccc(CO)cc1-c1nc2c(n1C(C)C)C(c1ccc(Cl)cc1C)N(c1cc(Cl)ccc1C)C(=O)N2]

The title compound was prepared in analogy to the procedure described for example 4 but using the product of step 11.1 and 8-bromo-6-(4-chloro-2-methylphenyl)-1-(5-chloro-2-methylphenyl)-7-isopropyl-6,7-dihydro-1H-purin-2(3H)-one (product of step 4.1). LCMS: (M+H)=565/567; t$_R$=1.18 min (LC-MS 1).

Step 11.1:
5-(Hydroxymethyl)-2-methoxyphenylboronic acid

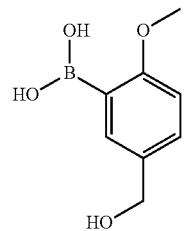

To a solution of 500 mg (2.78 mmol) 5-formyl-2methoxy-boronicacid in 45 ml MeOH, 158 mg (4.17 mmol) NaBH$_4$ was added and stirred for 0.5 hour. The reaction mixture was added to ice and extracted twice with EtOAc. The combined organic phases were dried over Na$_2$SO$_4$, filtered and evaporated to afford 273 mg (1.5 mmol, 54.0% yield) of the title compound as a colorless solid. 1H-NMR (MeOD, 400.13 MHz) δ ppm 9.86 (s, 1H) 7.35 (dd, 1H) 7.25 (m, 1H) 6.95 (d, 1H) 4.54 (s, 2H) 3.83 (s, 3H).

Example 12

3-[1-(5-Chloro-2-methyl-phenyl)-6-(4-chloro-2-methyl-phenyl)-7-isopropyl-2-oxo-2,3,6,7-tetrahydro-1H-purin-8-yl]-4-methoxy-benzonitrile

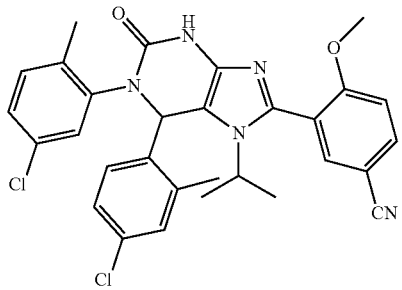 [SMILES: COc1ccc(C#N)cc1-c1nc2c(n1C(C)C)C(c1ccc(Cl)cc1C)N(c1cc(Cl)ccc1C)C(=O)N2]

The title compound was prepared in analogy to the procedure described for example 4 but using the product of step 12.1 and 8-bromo-6-(4-chloro-2-methylphenyl)-1-(5-chloro-2-methylphenyl)-7-isopropyl-6,7-dihydro-1H-purin-2(3H)-one (product of step 4.1). LCMS: (M+H)=560/562; t$_R$=1.22 min (LC-MS 1).

Step 12.1: 4-Methoxy-3-(4,4,5,5-tetramethyl-1,3,2-dioxaborolan-2-yl)benzonitrile

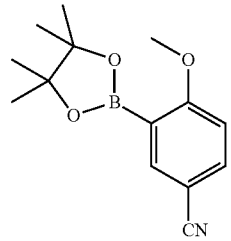 [SMILES: COc1ccc(C#N)cc1B1OC(C)(C)C(C)(C)O1]

To a solution of 3-bromo-4-methoxybenzonitrile (3 g, 14.15 mmol), bis(pinacolato)diboron (7.2 g, 28.4 mmol) and potassium acetate (4.2 g, 42.8 mmol) in DMSO (50 ml), PdCl2(dppf)-CH$_2$Cl$_2$ adduct (1.15 g, 1.408 mmol) were added under argon and the mixture was degassed and stirred at 100° C. for 3 hour. The reaction mixture was quenched with saturated NaHCO$_3$ and extracted with EtOAc. The organic phase was dried (Na$_2$SO$_4$), filtered and concentrated to dryness. The crude product was purified by chromatography (Silicagel, heptane, EtOAc). The pure fractions were recombined and concentrated under reduced pressure to give 3.46 g (13.09 mmol, 92% yield) of the title compound as a colourless oil. 1H-NMR (d6-DMSO, 400.13 MHz) δ ppm 7.92 (d, 1H) 7.80 (s, 1H) 7.14 (d, 1H) 3.82 (s, 3H) 1.26 (s, 12H).

The following examples were synthesized in analogy to the synthesis described for the previous examples using the appropriate available building blocks:

Example 13

4-[1-(5-Chloro-2-methyl-phenyl)-7-isopropyl-8-(2-methoxy-phenyl)-2-oxo-2,3,6,7-tetrahydro-1H-purin-6-yl]-benzonitrile

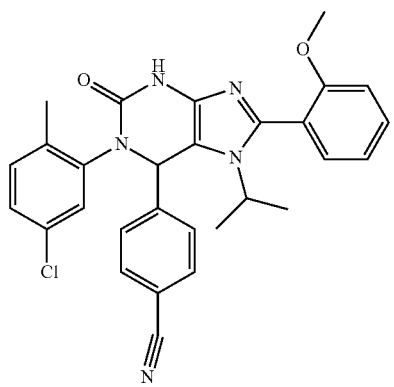

LCMS: (M+H)=512; t$_R$=1.14 min (LC-MS 1). HPLC: t$_R$=9.04 min (HPLC 4). 1H-NMR (d$_6$-DMSO, 600.13 MHz) Isomers mixture δ ppm 9.93, 9.77 (m, 1H) 7.86 (d, 1H) 7.79 (d, 1H) 7.46 (m, 1H) 7.72, 7.40-7.16 (m, 5H) 7.12 (m, 1H) 7.03, 5.99 (m, 2H) 6.32, 5.88 (m, 1H) 3.96-3.87 (m, 1H) 3.73 (bs, 3H) 2.28, 1.27 (m, 3H) 1.19-0.53 (m, 6H).

Example 14

4-(1-(3-Chloro-2-fluorophenyl)-7-isopropyl-8-(2-methoxyphenyl)-2-oxo-2,3,6,7-tetrahydro-1H-purin-6-yl)benzonitrile

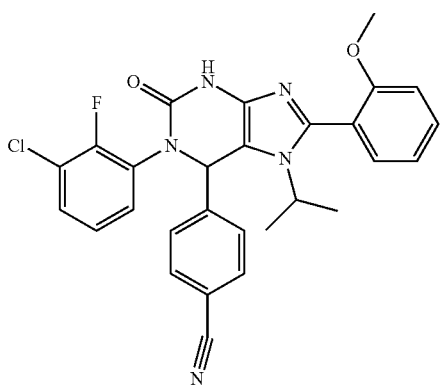

LCMS: (M+H)=516; t$_R$=1.07 min (LC-MS 4). HPLC: t$_R$=2.89 min (HPLC 5). 1H-NMR (d$_6$-DMSO, 400.13 MHz) δ ppm 9.98 (s, 1H) 7.81 (d, 2H) 7.49-7.09 (m, 8H) 7.01 (m, 1H) 6.19 (m, 1H) 3.92 (m, 1H) 3.73 (s, 3H) 1.15 (m, 3H) 0.56 (bs, 3H).

Example 15

6-(4-Chloro-3-fluorophenyl)-1-(3-chloro-4-fluorophenyl)-8-(2,4-dimethoxypyrimidin-5-yl)-7-isopropyl-6,7-dihydro-1H-purin-2(3H)-one

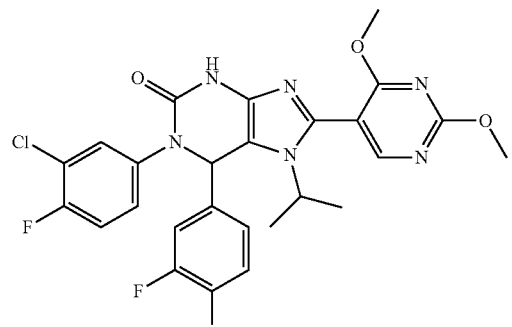

LCMS: (M+H)=575/577; t$_R$=1.13 min (LC-MS 4). HPLC: t$_R$=3.23 min (HPLC 5). 1H-NMR (d$_6$-DMSO, 600.13 MHz) 9.96 (s, 1H) 8.38 (s, 1H) 7.59 (t, 1H) 7.33 (m, 2H) 7.14 (d, 1H) 6.98 (d, 1H) 6.88 (bs, 1H) 6.20 (s, 1H) 4.00 (m, 1H) 3.95 (s, 3H) 3.90 (s, 3H) 1.16 (d, 3H) 0.67 (d, 3H).

Example 16

1-(5-Chloro-1-methyl-6-oxo-1,6-dihydro-pyridin-3-yl)-6-(4-chloro-2-methyl-phenyl)-8-(2,4-dimethoxypyrimidin-5-yl)-7-isopropyl-1,3,6,7-tetrahydro-purin-2-one

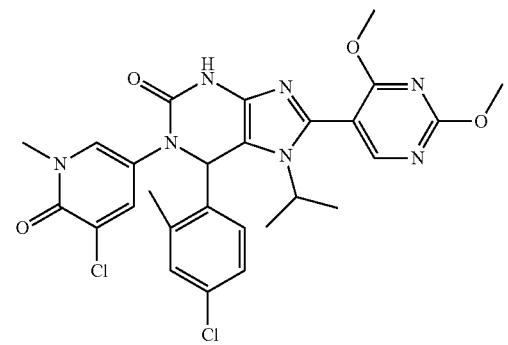 [SMILES: COc1ncc(-c2nc3c(n2C(C)C)C(c2ccc(Cl)cc2C)N(c2cc(Cl)c(=O)n(C)c2)C(=O)N3)c(OC)n1]

The product from step 16.1 was then subsequently used with the intermediate from step 4.4 and the product was synthesized according to the synthesis of previous examples using the appropriate available building blocks.

LCMS: (M+H)=584/586; t$_R$=0.97 min (LC-MS 1). 1H-NMR (d$_6$-DMSO, 400.13 MHz, 100° C.) isomers mixture δ ppm 9.68-9.54 (m, 1H) 8.32, 8.15 (m, 1H) 7.67-6.89 (m, 5H) 6.26 (m, 1H) 4.06 (m, 1H) 4.00 (s, 3H) 3.94 (s, 3H) 3.46 (s, 3H) 2.12-2.00 (m, 3H) 1.22-0.70 (m, 6H).

Step 16.1:
5-Amino-3-chloro-1-methyl-1H-pyridin-2-one

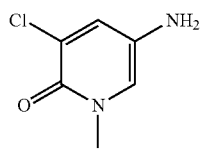

A solution of the product of step 16.2 (25.59 g, 136 mmol) and 19.5 g Ra—Ni (EtOH) in 400 ml methanol was shacked in a duck glass under H₂ atmosphere at RT for 97 hours. The reaction mixture was filtered over Celite and concentrated. The crude product was purified by chromatography (Silica-gel, CH₂Cl₂/MeOH 95:5) to afford 5.40 g (34.1 mmol, 25.09% yield) of the title compound as a dark solid. LCMS: (M+H)=159; $t_R$=0.33 min (LC-MS 1). TLC: Rf=0.28 (CH₂Cl₂/MeOH 9:1). 1H-NMR (d₆-DMSO, 400.43 MHz) δ ppm 7.36 (s, 1H) 6.89 (s, 1H) 4.42 (bs, 2H) 3.38 (s, 3H).

Step 16.2:
3-Chloro-1-methyl-5-nitro-1H-pyridin-2-one

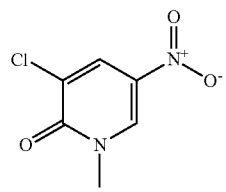

To a stirred suspension of 3-chloro-2-hydroxy-5-nitropyridine (25 g, 143 mmol) and K₂CO₃ (39.6 g, 286 mmol) in DMF (250 ml) under Ar, MeI (13.43 ml, 215 mmol) was added at 0° C. and the reaction mixture was stirred 3 hours at RT. The reaction mixture was concentrated, diluted with 300 ml water and extracted twice with 400 ml EtOAc. The combined organic layers were washed once with 200 ml water, dried (Na₂SO₄) and evaporated to afford 25.59 g (136 mmol, 95% yield) of the title compound as a yellow solid, which was used in the next steps without further purification. LCMS: (M+H)=189; $t_R$=0.64 min (LC-MS 1). 1H-NMR (d₆-DMSO, 400.43 MHz) δ ppm 9.23 (s, 1H) 8.45 (s, 1H) 3.61 (s, 3H).

Example 17

1-(5-Chloro-1-methyl-2-oxo-1,2-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one

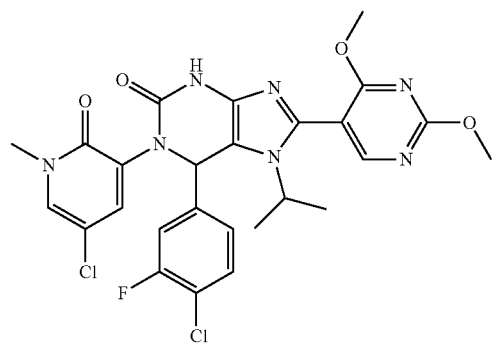

To a mixture of the product of step 17.1 (92 mg, 0.156 mmol) and 133 mg (0.626 mmol) K₃PO₄ in 1.2 ml 1,4-dioxane and 0.4 ml water, 11.45 mg (0.016 mmol) PdCl₂(dppf) and 38.4 mg (0.188 mmol) 2,4-dimethoxypyrimidin-5-ylboronic acid were added. The reaction mixture was heated at 100° C. for 3.5 hours. The reaction mixture was diluted with EtOAc. The organic phase was washed with water and brine, dried over Na₂SO₄, filtered and concentrated in vacuum. The crude material was solved in methanol and run through a cartridge (StratoSpheres SPE, PL3582-CM89, 500 mg per 6 ml tube 1.5 mmol (nominal)). After that the cartridge was rinsed 2× with methanol, the methanol fractions were combined and the solvent was evaporated. The residue was purified by preparative chromatography (Preparative Standard), then by preparative TLC (DCM/MeOH 9:1). The product was dissolved in 1,4-dioxane and freeze dried over night to obtain 7 mg (0.012 mmol, 7.53% yield) of the title compound as a colorless solid. LCMS: (M+H)=588/590; $t_R$=0.97 min (LC-MS 4). HPLC: $t_R$=2.80 min (HPLC 5). 1H-NMR (d₆-DMSO, 600.13 MHz) 9.93 (s, 1H) 8.40 (s, 1H) 8.04 (s, 1H) 7.59 (t, 1H) 7.17 (d, 1H) 6.99 (d, 1H) 6.90 (s, 1H) 6.12 (s, 1H) 4.00 (m, 1H) 3.95 (s, 3H) 3.91 (s, 3H) 3.48 (s, 3H) 1.20 (d, 3H) 0.68 (d, 3H).

Step 17.1: 8-Bromo-1-(5-chloro-1-methyl-2-oxo-1,2-dihydropyridin-3-yl)-6-(4-chloro-3-fluorophenyl)-7-isopropyl-6,7-dihydro-1H-purin-2(3H)-one

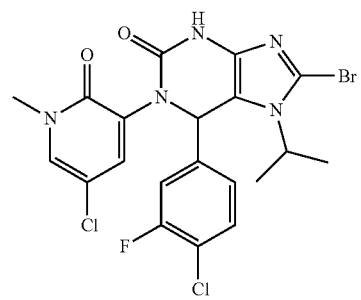 [SMILES: CC(C)n1c(Br)nc2c1C(c1ccc(Cl)c(F)c1)N(c1cc(Cl)cn(C)c1=O)C(=O)N2]

The title compound was obtained in analogy to the procedure described for the product of step 4.1 but using the product of step 17.2. After extraction the crude precipitate was treated with diethyl ether, kept in the sonic bath for 5 minutes and the precipitate was filtered off and dried under high vacuum to obtain a brown solid. LCMS: (M+H)=528/530; $t_R$=0.96 min (LC-MS 4). HPLC: $t_R$=2.93 min (HPLC 5). 1H-NMR (d₆-DMSO, 400 MHz) 9.94 (s, 1H) 8.00 (m, 1H) 7.55 (t, 1H) 7.20-7.15 (m, 1H) 7.00 (dd, 1H) 6.98 (m, 1H) 6.05 (s, 1H) 4.24 (m, 1H) 3.44 (s, 3H) 1.12 (d, 3H) 1.05 (d, 3H).

Step 17.2: 2-Bromo-5-((5-chloro-1-methyl-2-oxo-1,2-dihydropyridin-3-ylamino)(4-chloro-3-fluorophenyl)methyl)-1-isopropyl-1H-imidazole-4-carboxylic acid

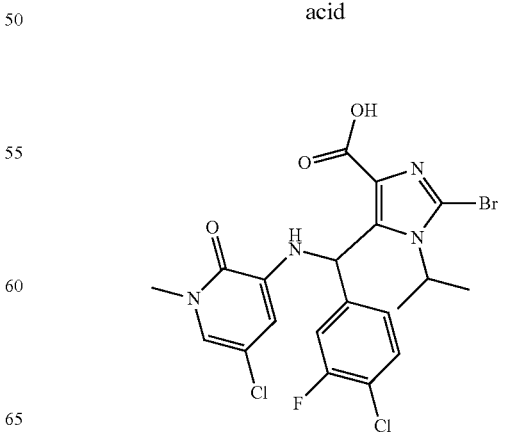

The title compound was prepared in analogy to the procedure described for the product of step 4.2 but using the product of step 17.3. LCMS: (M+H)=533; $t_R$=1.02 min (LC-MS 4). HPLC: $t_R$=3.08 min (HPLC 5). 1H-NMR ($d_6$-DMSO, 400 MHz) 12.90 (bs, 1H) 7.54 (bs, 1H) 7.29-7.22 (m, 2H) 7.00 (m, 1H) 6.87-6.58 (m, 2H) 6.50 (m, 1H) 4.73 (bs, 1H) 3.41 (s, 3H) 1.40-1.32 (m, 6H).

Step 17.3: Ethyl 2-bromo-5-((5-chloro-1-methyl-2-oxo-1,2-dihydropyridin-3-ylamino)(4-chloro-3-fluorophenyl)methyl)-1-isopropyl-1H-imidazole-4-carboxylate

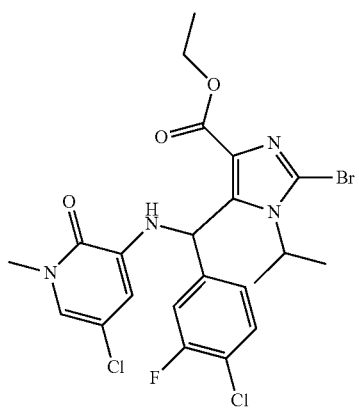 [SMILES: CCOC(=O)c1nc(Br)n(C(C)C)c1C(Nc1cc(Cl)cn(C)c1=O)c1ccc(Cl)c(F)c1]

To a solution of the product of step 17.4 in 15 ml $CH_2Cl_2$ at 0° C., $Et_3N$ (1.4 ml, 10.10 mmol) and $Ms_2O$ (703 mg, 4.04 mmol) were added and the mixture was stirred at 0° C. for 45 min. Then the product of step 17.5 in 4 ml $CH_2Cl_2$ was added and the mixture was stirred at RT for 15 h. The reaction mixture was diluted with EtOAc and extracted with a saturated $NaHCO_3$ solution. The organic layer was washed with brine, dried ($Na_2SO_4$), filtered and concentrated. The crude product was treated with diethyl ether, kept in the sonic bath for 5 minutes and the precipitate was filtered off and dried under high vacuum to obtain the title product as grey solid. LCMS: (M+H)=559/561; $t_R$=1.23 min (LC-MS 4). HPLC: $t_R$=3.60 min (HPLC 5). 1H-NMR ($d_6$-DMSO, 400 MHz) 7.55 (bs, 1H) 7.24 (m, 2H) 7.00 (m, 1H) 6.63 (m, 2H) 6.44 (bs, 1H) 4.72 (m, 1H) 4.18 (m, 2H) 3.41 (s, 3H) 1.41-1.13 (m, 9H).

Step 17.4: Ethyl 2-bromo-5-((4-chloro-3-fluorophenyl)(hydroxy)methyl)-1-isopropyl-1H-imidazole-4-carboxylate

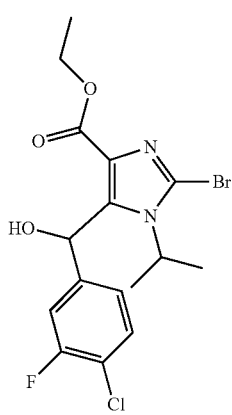 [SMILES: CCOC(=O)c1nc(Br)n(C(C)C)c1C(O)c1ccc(Cl)c(F)c1]

To a solution of the product of step 4.6 (9.47 g, 36.3 mmol) in 176 ml THF cooled to −78° C., 28.2 ml (50.8 mmol) of a 1.8M LDA in heptane solution was added slowly (over 15 min). The reaction mixture was stirred at −78° C. for 2 h 50. Then a solution of 8.05 g (50.8 mmol) 4-chloro-3-fluorobenzaldehyde in 40 ml THF was added over 20 min. The brown suspension was stirred at −78° C. for 30 min, and then allowed to warm up to −20° C. in 1 hour. The mixture was stirred at between −20° C. and −8° C. for 1 h 10, then cooled again to −20° C. and quenched with 4.98 ml (87 mmol) acetic acid. The reaction mixture was taken into EtOAc/water. The phases were separated and the organic phase was washed with water and brine. The organic phase was dried on $Na_2SO_4$, filtered and evaporated. By reducing the volume, crystals were precipitated. They were filtered and washed with heptanes, then dried overnight under vacuum to give 12.33 g (29.4 mmol, 81% yield) of the title compound as beige crystals. LCMS: (M+H)=419/421; $t_R$=1.14 min (LC-MS 4). HPLC: $t_R$=3.39 min (HPLC 5). 1H-NMR ($d_6$-DMSO, 400 MHz) δ ppm 7.58 (m, 1H) 7.36 (d, 1H) 7.05 (d, 1H) 6.88 (m, 2H) 4.69 (quin, 1H) 4.27 (m, 2H) 1.48 (d, 3H) 1.29 (t, 3H) 0.97 (d, 3H).

Step 17.5:
3-Amino-5-chloro-1-methylpyridin-2(1H)-one

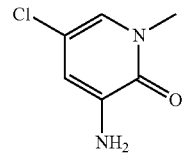

A solution of the product of step 17.6 (14.63 g, 78 mmol) and 4.0 g Ra—Ni (EtOH) in 300 ml methanol was shacked at RT under $H_2$ atmosphere for 8 hours. The reaction mixture was filtered through Celite and evaporated to dryness to afford 12.67 g (77 mmol, 100% yield) of the title compound as a thick oil. LCMS: (M+H)=159; $t_R$=0.51 min (LC-MS 4). HPLC: $t_R$=1.71 min (HPLC 5). 1H-NMR ($d_6$-DMSO, 400 MHz) δ ppm 7.06 (s, 1H) 6.34 (s, 1H) 5.45 (s, 2H) 3.37 (s, 3H).

Step 17.6:
5-Chloro-1-methyl-3-nitropyridin-2(1H)-one

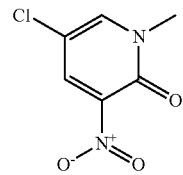

A solution of 5-chloro-2-hydroxy-3-nitropyridine (15.0 g, 86 mmol) in DMF (200 ml) was cooled down to 0° C. under argon. Then NaH (4.13 g, 103 mmol) was added by portions in 25 min and the reaction mixture was stirred at 0° C. for 1 hour. After that $CH_3I$ (8.06 ml, 129 mmol) was added dropwise and the ice-bath was removed. The reaction mixture was stirred at RT for 4 hours. The solution was concentrated and then the slurry mixture was taken in 250 ml water and extracted twice with 300 ml ethyl acetate. The combined organic phases were washed twice with 200 ml brine, dried (Na$_2$SO$_4$) and evaporated to dryness to afford 14.63 g (78 mmol, 90% yield) of the title compound as dark yellow solid. LCMS: (M+H)=189; t$_R$=0.55 min (LC-MS 4). HPLC: t$_R$=1.77 min (HPLC 5). $^1$H-NMR (d$_6$-DMSO, 400 MHz) δ ppm 8.53 (s, 2H) 3.52 (s, 3H).

The following two examples were synthesized in analogy to previous examples and using the building blocks prepared in examples 16 and 17 and using the appropriate building blocks:

Example 18

1-(5-Chloro-1-methyl-2-oxo-1,2-dihydropyridin-3-yl)-6-(4-chlorophenyl)-8-(2,4-dimethoxypyrimidin-5-yl)-7-isopropyl-6,7-dihydro-1H-purin-2(3H)-one

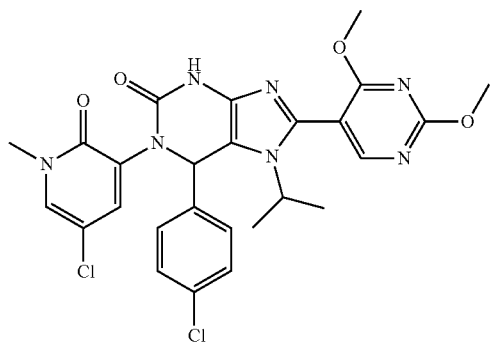

LCMS: (M+H)=570/572; t$_R$=0.96 min (LC-MS 4). 1H-NMR (d6-DMSO, 400 MHz) 9.90 (m, 1H) 8.39 (s, 1H) 8.04 (m, 1H) 7.43 (m, 2H) 7.16 (d, 2H) 6.78 (m, 1H) 6.14 (m, 1H) 4.00-3.90 (m, 7H) 3.50 (s, 3H) 1.22 (m, 3H) 0.67 (d, 3H).

Example 19

1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one

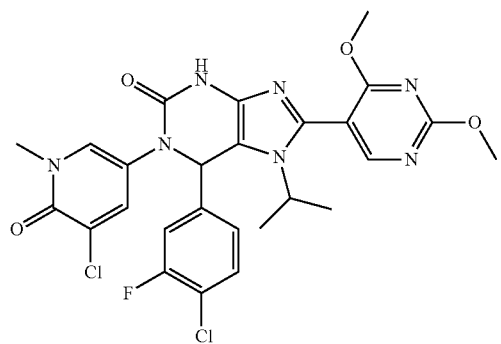

LCMS: (M+H)=588/590; t$_R$=0.92 min (LC-MS 4). HPLC: t$_R$=2.70 min (HPLC 5). 1H-NMR (d6-DMSO, 400.13 MHz) δ ppm 9.99 (s, 1H) 8.39 (s, 1H) 7.68-7.62 (m, 2H) 7.25 (dd, 1H) 7.13 (m, 1H) 7.09 (d, 1H) 6.10 (s, 1H) 4.00 (m, 1H) 3.97 (s, 3H) 3.92 (s, 3H) 3.46 (s, 3H) 1.23 (d, 3H) 0.68 (d, 3H).

Example 20

1-(5-Chloro-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one

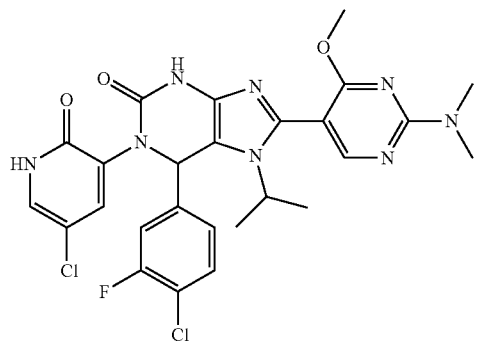 [SMILES: COc1nc(N(C)C)ncc1-c1nc2c(n1C(C)C)C(c1ccc(Cl)c(F)c1)N(c1cc(Cl)c[nH]c1=O)C(=O)N2]

The product of step 20.1 (90 mg, 0.121 mmol) was solved in 1 ml TFA. The reaction mixture was heated at 100° C. for 30 min by microwave. The reaction mixture was concentrated. The residue was diluted with EtOAc and saturated NaHCO$_3$ solution. The water phase was extracted twice with EtOAc. The organic phases were combined and washed with water and brine, dried over Na$_2$SO$_4$, filtered and concentrated in vacuum to obtain the black crude material. The crude product was purified by preparative HPLC (Prep HPLC Method 1, gradient: 20 to 70% B in 20 minutes). The fractions containing the product were combined and worked up (addition of NaHCO$_3$, removal of acetonitrile followed by extraction with EtOAc). The residue was dissolved in 1,4-dioxane and freeze dried to obtain 13 mg (0.022 mmol, 17.95% yield) of the title compound as a yellowish solid. LCMS: (M+H)=587/589; t$_R$=0.99 min (LC-MS 4). HPLC: t$_R$=2.49 min (HPLC 5). 1H-NMR (d6-DMSO, 600.13 MHz) 12.26 (bs, 1H) 9.75 (s, 1H) 8.11 (s, 1H) 7.61 (d, 1H) 7.57 (t, 1H) 7.10 (d, 1H) 6.97 (d, 1H) 6.86 (m, 1H) 6.20 (s, 1H) 3.98 (quin, 1H) 3.85 (s, 3H) 3.15 (s, 6H) 1.21 (d, 3H) 0.68 (d, 3H).

Step 20.1: 1-(5-Chloro-1-(4-methoxybenzyl)-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one

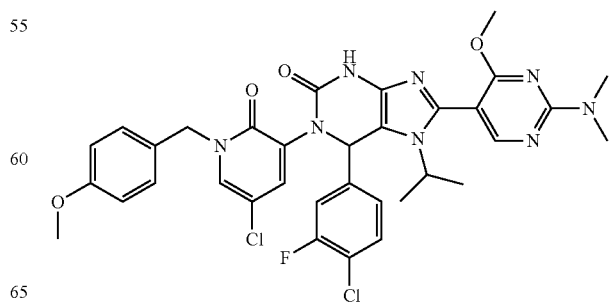

The title compound was obtained in analogy to the procedure described for example 17 but using the product of step 20.1 and the product of step 20.7. After the extraction and the filtration, the residue was purified by preparative chromatography (Prep HPLC Method 1, gradient: 20 to 70% B in 20 minutes). LCMS: (M+H)=707/709; $t_R$=1.20 min (LC-MS 4). HPLC: $t_R$=2.93 min (HPLC 5). 1H-NMR (d6-DMSO, 400 MHz) 9.81 (s, 1H) 8.09 (s, 1H) 8.07 (d, 1H) 7.53 (t, 1H) 7.20 (d, 2H) 7.10 (m, 2H) 6.95 (d, 1H) 6.89 (d, 2H) 6.13 (s, 1H) 5.22 (d, 1H) 4.83 (d, 1H) 3.96 (m, 1H) 3.84 (s, 3H) 3.72 (s, 3H) 3.14 (s, 6H) 1.18 (d, 3H) 0.65 (d, 3H).

Step 20.2: 8-Bromo-1-(5-chloro-1-(4-methoxybenzyl)-2-oxo-1,2-dihydropyridin-3-yl)-6-(4-chloro-3-fluorophenyl)-7-isopropyl-6,7-dihydro-1H-purin-2(3H)-one

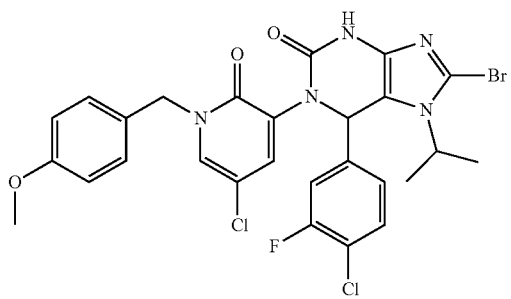 [SMILES: COc1ccc(Cn2cc(Cl)cc(N3C(=O)Nc4nc(Br)n(C(C)C)c4C3c3ccc(Cl)c(F)c3)c2=O)cc1]

The title compound was obtained in analogy to the procedure described for step 17.1 but using the product of 20.3. LCMS: (M+H)=636; $t_R$=1.13 min (LC-MS 4). HPLC: $t_R$=3.33 min (HPLC 5). 1H-NMR ($d_6$-DMSO, 400 MHz) 9.91 (s, 1H) 8.03 (m, 1H) 7.51 (t, 1H) 7.14 (m, 4H) 6.96 (d, 1H) 6.87 (d, 2H) 6.12 (s, 1H) 5.14 (d, 1H) 4.79 (d, 1H) 4.20 (m, 1H) 3.72 (s, 3H) 1.09-1.04 (m, 6H).

Step 20.3: 2-Bromo-5-((5-chloro-1-(4-methoxybenzyl)-2-oxo-1,2-dihydropyridin-3-ylamino)(4-chloro-3-fluorophenyl)methyl)-1-isopropyl-1H-imidazole-4-carboxylic acid

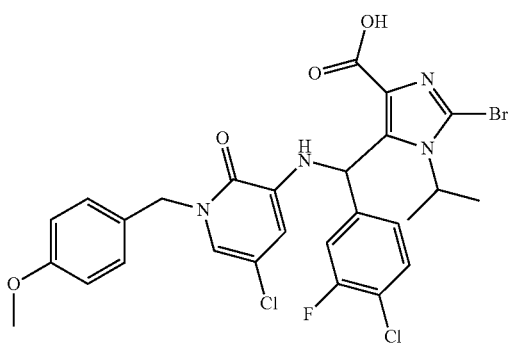 [SMILES: COc1ccc(Cn2cc(Cl)cc(NC(c3ccc(Cl)c(F)c3)c3c(C(=O)O)nc(Br)n3C(C)C)c2=O)cc1]

The title compound was prepared in analogy to the procedure described for step 17.2 but using the product of step 20.4 to afford the title compound as a brown amorphous solid, which was used in the next steps without purification. LCMS: (M+H)=639; $t_R$=1.19 min (LC-MS 4). HPLC: $t_R$=3.51 min (HPLC 5). 1H-NMR ($d_6$-DMSO, 400 MHz) 7.53 (m, 1H) 7.29-7.20 (m, 5H) 7.15 (m, 1H) 7.04 (m, 1H) 6.86 (m, 1H) 6.52 (m, 1H) 4.98 (m, 2H) 3.68 (s, 3H) 2.26 (s, 2H) 1.36-1.29 (m, 6H).

Step 20.4: Ethyl 2-bromo-5-((5-chloro-1-(4-methoxybenzyl)-2-oxo-1,2-dihydropyridin-3-ylamino)(4-chloro-3-fluorophenyl)methyl)-1-isopropyl-1H-imidazole-4-carboxylate

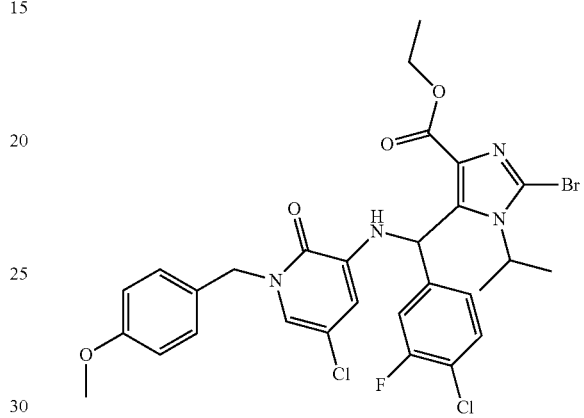

The title compound was prepared in analogy to the procedure described for step 17.3 but using the product from step 17.4 and the product from step 20.5. After extraction, the crude product was purified by chromatography (Silicagel, heptane, EtOAc) to obtain an amorphous solid. LCMS: (M+H)=665/667/669; $t_R$=1.37 min (LC-MS 4). HPLC: $t_R$=3.97 min (HPLC 5).

Step 20.5: 3-Amino-5-chloro-1-(4-methoxybenzyl)pyridin-2(1H)-one

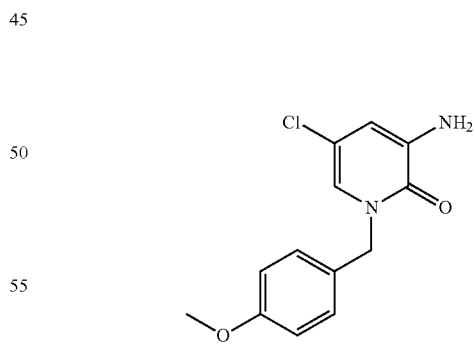

A solution of the product of step 20.6 (11.58, 39.3 mmol) in 400 ml methanol/THF 1:1 containing 3.5 g Ra—Ni (EtOH) was shacked under $H_2$ atmosphere at RT for 20.5 hours. The reaction mixture was filtered through Celite and evaporated to dryness to afford 10.6 g (39.3 mmol, 93% yield) of the title compound as a dark brownish resin. LCMS: (M+H)=265; $t_R$=0.87 min (LC-MS 4).

Step 20.6: 5-Chloro-1-(4-methoxybenzyl)-3-nitropyridin-2(1H)-one

Step 20.8: 5-Bromo-4-methoxy-N,N-dimethylpyrimidin-2-amine

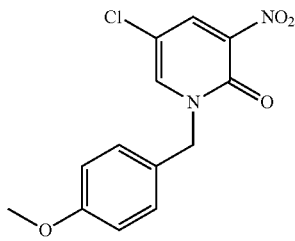 [SMILES: COc1ccc(Cn2cc(Cl)cc([N+](=O)[O-])c2=O)cc1]

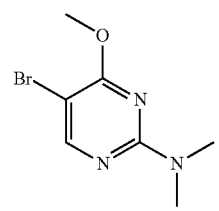

To a stirred solution of 5-chloro-3-nitropyridin-2-ol (12 g, 68.8 mmol) in DMF (80 ml) was added in several portions NaH (3.30 g, 83 mmol) at 0° C. The reaction mixture was stirred in the ice-bath for 2 hours. Then 4-methoxybenzyl chloride (11.19 ml, 83 mmol) was added and the reaction mixture was heated at 80° C. for 1 hour. The reaction mixture was quenched with aqueous saturated NaHCO₃ solution and extracted twice with EtOAc. The organic layers were washed with brine, combined, dried over sodium sulphate, filtered and evaporated. The crude material was taken up in n-heptane/AcOEt 10:1 and the suspension was kept in the sonic bath for 10 minutes. After filtration the filtrate was washed with n-heptane and dried in vacuum to obtain 11.84 g (40.2 mmol, 58.4% yield) of the title compound as a greenish solid. LCMS: (M+H)=295; $t_R$=0.94 min (LC-MS 4). 1H-NMR ($d_6$-DMSO, 400 MHz) 8.72 (d, 1H) 8.56 (d, 1H) 7.36 (d, 2H) 6.94 (d, 2H) 5.13 (s, 2H) 3.74 (s, 3H).

Step 20.7: 4-Methoxy-N,N-dimethyl-5-(4,4,5,5-tetramethyl-1,3,2-dioxaborolan-2-yl)pyrimidin-2-amine

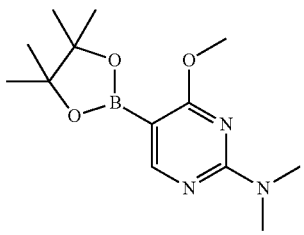

To a solution of the product of step 20.8 (5 g, 21.54 mmol) in 157 ml dioxane, 7.11 g (28.0 mmol) bis(pinacolato) diboron and 6.34 g (64.6 mmol) potassium acetate were added and the solution was heated at 110° C. 1.76 g (2.154 mmol) PdCl₂(dppf)-CH₂Cl₂ adduct was added and the mixture was stirred for 4.5 hours. The mixture was filtered, washed with toluene and evaporated to give 10.6 g (11.39 mmol, 52.9% yield) of the title compound as a black solid. The product was directly used in the next step.

224 ml (448 mmol) of dimethylamine was added to a solution of 50 g (224 mmol) 5-bromo-2-chloro-4-methoxypyrimidine at RT and the solution was stirred at RT for 72 hours. To get more product, another 40 ml dimethylamine were added and reaction mixture was stirred at RT for 1 hour. The mixture was concentrated and the crude was diluted in EtOAc/brine, extracted and the organic extract was dried (Na₂SO₄) and concentrated to afford 51.79 g (223 mmol) of the title compound as a white solid. LCMS: (M+H)=231/233; $t_R$=1.02 min (LC-MS 4). 1H-NMR ($d_6$-DMSO, 400 MHz) 8.17 (s, 1H) 3.89 (s, 3H) 3.07 (s, 6H).

Example 21

8-(2-Amino-4-methoxypyrimidin-5-yl)-1-(5-chloro-1-methyl-2-oxo-1,2-dihydropyridin-3-yl)-6-(4-chlorophenyl)-7-isopropyl-6,7-dihydro-1H-purin-2(3H)-one

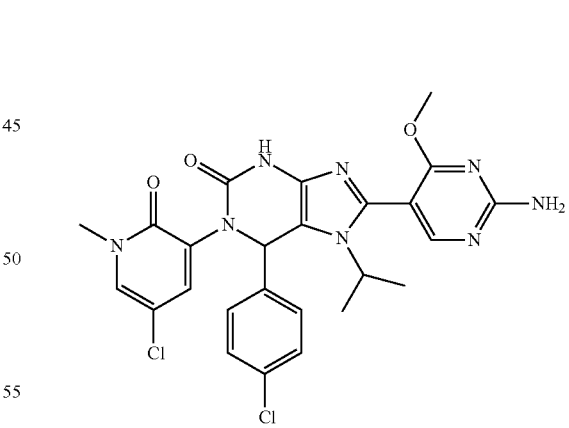

The title compound was obtained in analogy to the procedure described for example 17 but using the product of step 21.1 and the product of step 21.2. LCMS: (M+H)=555/557; $t_R$=0.84 min (LC-MS 4). 1H-NMR ($d_6$-DMSO, 400 MHz) 9.82 (s, 1H) 8.04 (m, 1H) 8.00 (s, 1H) 7.43 (d, 2H) 7.14 (d, 2H) 6.95 (s, 2H) 6.77 (d, 1H) 6.13 (s, 1H) 4.00 (m, 1H) 3.81 (s, 3H) 3.51 (s, 3H) 1.22 (d, 3H) 0.67 (d, 3H).

Step 21.1: 8-Bromo-1-(5-chloro-1-methyl-2-oxo-1,2-dihydropyridin-3-yl)-6-(4-chlorophenyl)-7-isopropyl-6,7-dihydro-1H-purin-2(3H)-one

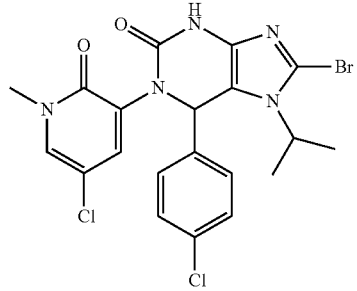 [SMILES: CC(C)n1c(Br)nc2c1C(c1ccc(Cl)cc1)N(c1cc(Cl)cn(C)c1=O)C(=O)N2]

The title compound was obtained in analogy to the procedures described for the synthesis of example 17 but in step 17.4 4-chlorobenzaldehyde was used. After extraction, the crude was triturated with Et$_2$O and the solid filtered to afford 148 mg (0.217 mmol, 100% yield) as a light yellow solid. LCMS: (M+H)=512; t$_R$=0.95 min (LC-MS 4).

Step 21.2: 4-Methoxy-5-(4,4,5,5-tetramethyl-1,3,2-dioxaborolan-2-yl)pyrimidin-2-amine

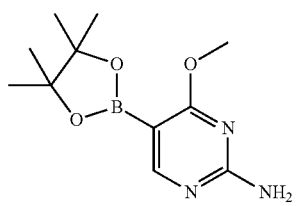 [SMILES: COc1nc(N)ncc1B1OC(C)(C)C(C)(C)O1]

A solution of 9.95 g (48.8 mmol) 5-bromo-4-methoxypyrimidin-2-amine, 13.62 g (53.6 mmol) Bis(pinacolato)diboron, 14.36 g (146 mmol) potassium acetate, 3.98 g (4.88 mmol) PdCl$_2$(dppf)-CH$_2$Cl$_2$ adduct was stirred at 110° C. for 12 hr. After that the reaction mixture was diluted in toluene, sonicated and filtered. The cake was rinsed with hot toluene and concentrated to afford 20.12 g (24.04 mmol, 49.3% yield) of the title compound as a brown solid. 1H-NMR (CDCl3, 400 MHz) 8.38 (s, 1H) 5.69 (s, 2H) 3.92 (s, 3H) 12.27 (m, 12H).

The following examples were synthesized in analogy to previously described examples using described building blocks (e.g. example 20 and 21) and using the appropriate building blocks:

Example 22

1-(5-Chloro-1-methyl-2-oxo-1,2-dihydropyridin-3-yl)-6-(4-chlorophenyl)-8-(2-(dimethylamino)-4-methoxypyrimidin-5-yl)-7-isopropyl-6,7-dihydro-1H-purin-2(3H)-one

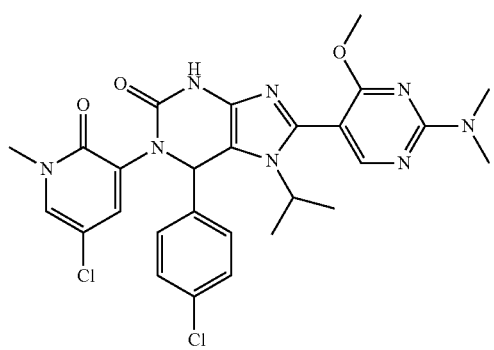

LCMS: (M+H)=583/585; t$_R$=1.04 min (LC-MS 4). 1H-NMR (d$_6$-DMSO, 400 MHz) 9.83 (s, 1H) 8.11 (s, 1H) 8.03 (d, 1H) 7.42 (d, 2H) 7.14 (d, 2H) 6.76 (d, 1H) 6.12 (s, 1H) 3.98 (m, 1H) 3.86 (s, 3H) 3.50 (s, 3H) 3.16 (s, 6H) 1.22 (d, 3H) 0.66 (d, 3H).

Example 23

6-(4-Chloro-3-fluorophenyl)-1-(3-chloro-4-fluorophenyl)-8-(2-(dimethylamino)-4-methoxypyrimidin-5-yl)-7-isopropyl-6,7-dihydro-1H-purin-2(3H)-one

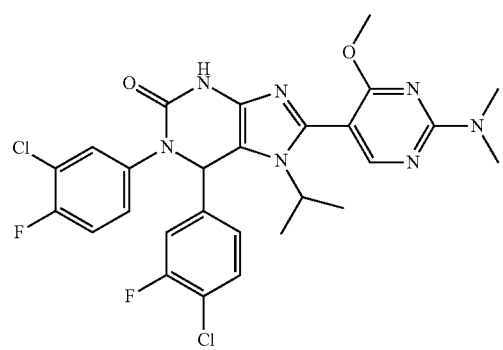 [SMILES: COc1nc(N(C)C)ncc1-c1nc2c(n1C(C)C)C(c1ccc(Cl)c(F)c1)N(c1ccc(F)c(Cl)c1)C(=O)N2]

LCMS: (M+H)=588/590; t$_R$=1.22 min (LC-MS 4). HPLC: t$_R$=2.96 min (HPLC 5). 1H-NMR (d6-DMSO, 600.13 MHz) 9.91 (s, 1H) 8.11 (s, 1H) 7.60 (t, 1H) 7.34 (m, 2H) 7.12 (d, 1H) 6.99 (d, 1H) 6.90 (m, 1H) 6.20 (s, 1H) 4.00 (m, 1H) 3.86 (s, 3H) 3.17 (s, 6H) 1.19 (d, 3H) 0.68 (d, 3H).

Example 24

1-(5-Chloro-1-methyl-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one

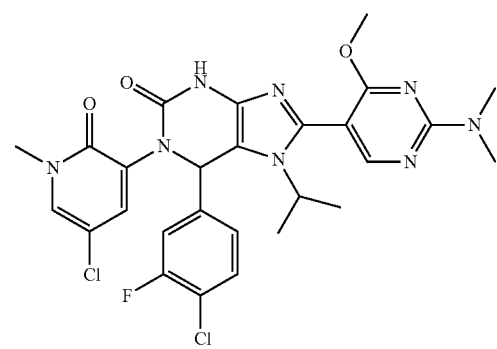

LCMS: (M+H)=601/603; t$_R$=1.07 min (LC-MS 4). HPLC: t$_R$=2.60 min (HPLC 5). 1H-NMR (d6-DMSO, 600.13 MHz) 9.86 (s, 1H) 8.12 (s, 1H) 8.04 (s, 1H) 7.58 (t, 1H) 7.16 (d, 1H) 6.99 (d, 1H) 6.88 (s, 1H) 6.10 (s, 1H) 3.98 (m, 1H) 3.85 (s, 3H) 3.48 (s, 3H) 3.15 (s, 6H) 1.21 (d, 3H) 0.68 (d, 3H).

Example 25

1-(5-Chloro-2-oxo-1,2-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one

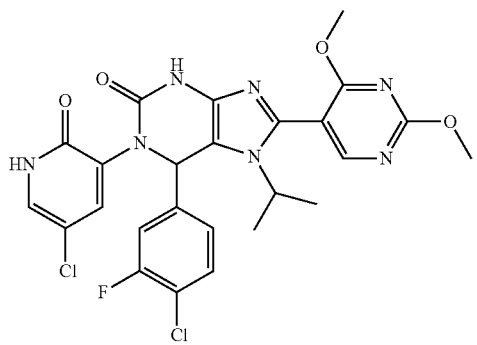 [SMILES: COc1ncc(-c2nc3c(n2C(C)C)C(c2ccc(Cl)c(F)c2)N(c2cc(Cl)c[nH]c2=O)C(=O)N3)c(OC)n1]

LCMS: (M+H)=574/576; $t_R$=0.93 min (LC-MS 4). HPLC: $t_R$=2.73 min (HPLC 5). 1H-NMR (d6-DMSO, 600.13 MHz) δ ppm 9.43 (s, 1H) 8.38 (s, 1H) 7.54 (t, 1H) 7.49 (s, 1H) 6.86 (d, 1H) 6.82 (d, 1H) 6.62 (s, 1H) 6.41 (m, 1H) 3.99 (m, 1H) 3.95 (s, 3H) 3.91 (s, 3H) 1.26 (d, 3H) 0.69 (d, 3H).

In another embodiment, the invention provides a compound as described herein.

Time Resolved Fluorescence Energy Transfer (TR-FRET) Assay

The inhibition of p53-MDM2 and p53-MDM4 interactions is measured by time resolved fluorescence energy transfer (TR-FRET). Fluorescence energy transfer (or Foerster resonance energy transfer) describes an energy transfer between donor and acceptor fluorescent molecules. For this assay, human MDM2 protein (amino acids 2-188) and human MDM4 protein (amino acids 2-185), tagged with a C-terminal biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor molecule at 340 nm, binding interaction between MDM2 or MDM4 and the p53 peptide induces energy transfer and enhanced response at the acceptor emission wavelength at 665 nm.

Disruption of the formation of the p53-MDM2 or p53-MDM4 complex due to an inhibitor molecule binding to the p53 binding site of MDM2 or MDM4 results in increased donor emission at 620 nm. The ratiometric FRET assay readout is calculated from the raw data of the two distinct fluorescence signals measured in time resolved mode (fluorescence 665 nm/fluorescence 620 nm×1000).

The test is performed in white 384-well plates (Greiner Bio-One, reference 781207) in a total volume of 60 µL by adding 1 µL of compounds tested at different concentrations diluted in 100% DMSO (1.7% final DMSO concentration) in reaction buffer (PBS, 125 mM NaCl, 0.001% Novexin (consists of carbohydrate polymers), designed to increase the solubility and stability of proteins; Expedeon Ltd., Cambridgeshire, United Kingdom), 0.01% Gelatin, 0.01% 0.2%, Pluronic F-127 (block copolymer from ethylenoxide and propyleneoxide), 1 mM DTT). After addition of 1.25 nM MDM2-biotinylated or 2.5 nM MDM4-biotinylated (internal preparations, both MDM2 and MDM4 are biotinylated at the C-terminal of the peptide construct), and 0.625 nM Europium labeled streptavidin (Perkin Elmer), the solution is pre-incubated for 15 minutes at room temperature, then 10 nM Cy5-p53 peptide (internal preparation, the Cy5 dye is directly bound to the N-terminal part of p53 peptide construct) is added before an incubation at room temperature for 15 minutes prior to reading the plate. For measurement of samples, a Victor II microplate reader (Perkin Elmer) is used with the following settings: Excitation 340 nm, Emission Donor 620 nm and Emission Acceptor 665 nm. $IC_{50}$ values are calculated by curve fitting using XLfit. If not specified, reagents are purchased from Sigma-Aldrich Chemie GmBH, Buchs, Switzerland.

This assay was used to evaluate compounds displaying inhibition of p53-MDM2 interaction and p53-MDM4 interaction at $IC_{50}$s of 0.005 to 50 µM (p53-MDM2 Assay 1 and p53-MDM4 Assay 1, respectively). For selected compounds displaying $IC_{50}$s between 0.05 and 5 nM on MDM2, a slightly modified assay is used with the following adaptations: 0.1 nM MDM2, 0.1 nM Europium labeled streptavidin and Tecan genios Pro is used as a microplate reader for the fluorescence measurements (p53-MDM2 Assay 2).

TABLE

| | $IC_{50}$ (µM) | | $IC_{50}$ (nM) |
|---|---|---|---|
| Example | p53-MDM2 Assay 1 | p53-MDM4 Assay 1 | p53-MDM2 Assay 2 |
| 1 | 0.0020 | 1.51 | 0.882 |
| 2 | 0.0021 | 2.13 | 0.779 |
| 3 | 0.0018 | 1.45 | n.d. |
| 4 | 0.0031 | 16.69 | n.d. |
| 5 | 0.12 | n.d. | n.d. |
| 6 | 0.0085 | 14.04 | n.d. |
| 7 | n.d. | n.d. | 0.531 |
| 8 | n.d. | n.d. | 0.447 |
| 9 | n.d. | n.d. | 0.21 |
| 10 | n.d. | n.d. | 0.432 |
| 11 | n.d. | n.d. | 0.371 |
| 12 | n.d. | n.d. | 0.414 |
| 13 | n.d. | n.d. | 0.724 |
| 14 | n.d. | n.d. | 0.473 |
| 15 | n.d. | n.d. | 0.451 |
| 16 | n.d. | n.d. | 3.106 |
| 17 | n.d. | n.d. | 1.668 |
| 18 | n.d. | n.d. | 2.914 |
| 19 | n.d. | n.d. | 0.93 |
| 20 | n.d. | n.d. | 0.354 |
| 21 | n.d. | n.d. | 4.298 |
| 22 | n.d. | n.d. | 0.587 |
| 23 | n.d. | n.d. | 0.385 |
| 24 | n.d. | n.d. | 0.748 |
| 25 | n.d. | n.d. | 0.356 | n.d.: not determined

Cellular Proliferation Assay in SJSA-1 and SAOS-2 Cells Based on YO-PRO®-1 Iodide Staining The effect of PPI (protein-protein interaction) inhibitors on cell growth of p53 wild-type or mutant cells is assessed in a proliferation assay based on YO-PRO®-1 iodide staining (J Immunol Methods. 1995; 185(2):249-58). The principal of this assay is the use of the DNA-intercalating dye YO-PRO®-1 iodide which upon binding to DNA emits a strong fluorescence signal. In addition, the dye is membrane-impermeant and thus, apoptotic cells can be distinguished from the viable cell population during the same assay. In the absence of cell permeabilization, the dye is only entering into cells that are beginning to undergo apoptosis. After treatment of the cells with a lysis buffer, the total cell number can be estimated.

To test PPI inhibitors on cell growth, SJSA-1 cells (p53 wild-type cells) and SAOS-2 cells (p53 null cells) are plated out into 96-well micro-titer plates and treated with decreasing concentrations of the compounds. After a 72 hour incubation period, 2.5 μM YO-PRO®-1 iodide is directly added to the cells and a first read-out is performed using a standard fluorescence plate reader (filter setting 485/530 nm) revealing the relative number of apoptotic cells. Subsequently, cells are permeabilized by directly adding lysis buffer containing the detergent NP40, EDTA and EGTA to obtain final concentrations of 0.01% and 5 mM, respectively. After complete permeabilization, the total cell number is quantified during a second read using the fluorescence plate reader with the same settings.

In Vivo Experiments

There are also experiments that can demonstrate the anti-tumor activity of compounds of the formula (I) in vivo. For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoroethyldifluormethylether, Abbot, Wiesbaden, Germany) narcosis, 3×10$^6$ cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated.

As an alternative to cell line SJSA-1, other cell lines may also be used in the same manner, for example,

- the HCT116 colon carcinoma cell line (ATCC No. CCL-247);
- the LNCaP clone FGC prostate carcinoma cell line (ATCC No. CRL-1740);
- the RKO colon carcinoma cell line (ATCC No. CRL-2577);
- the HT1080 fibrosarcoma cell line (ATCC No. CCL-121);
- the A375 malignant melanoma cell line (ATCC No. CRL-1619),
- the NCI-H460 large cell lung carcinoma cell line (ATCC No. HTB-177);
- the JEG-3 choriocarcinoma (ATCC No. HTB-36)
- the ZR-75-1 breast ductal carcinoma (ATCC No. CRL-1500)

The invention claimed is:

1. A compound of formula (I), or a salt thereof,

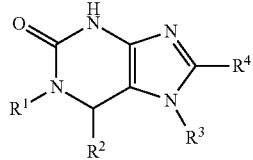

(I)

wherein
R$^1$ is
(a) a phenyl substituted with one to five substituents each independently selected from halo, (C$_1$-C$_4$)alkyl and —O—(CH$_2$)$_n$—N(CH$_3$)$_2$, wherein n is 1 or 2; or
(b) a 6-oxo-1,6-dihydropyridin-3-yl having Formula (Ia) or a 2-oxo-1,2-dihydropyridin-3-yl having Formula (Ib),

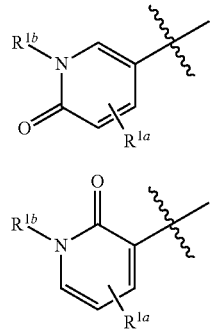

wherein R$^{1a}$ is H, halo or (C$_1$-C$_4$)alkyl, and R$^{1b}$ is H, (C$_1$-C$_4$)alkyl, —(CH$_2$)$_m$—N(CH$_3$)$_2$, or —(CH$_2$)$_m$—OR$^{1c}$, where R$^{1c}$ is H or (C$_1$-C$_4$)alkyl, and m is 1 or 2;

R$^2$ is a phenyl substituted with one substituent in the para position selected from chloro, fluoro, trifluoromethyl, methyl and cyano and optionally one additional substituent selected from halo and (C$_1$-C$_4$)alkyl-, optionally substituted with (C$_1$-C$_4$)alkoxy;

R$^3$ is selected from isopropyl, cyclopropyl, isobutyl, cyclobutyl and cyclopentyl;

R$^4$ is halo, —(CH$_2$)$_q$-pyridyl, —(CH$_2$)$_q$-pyrimidyl, —(CH$_2$)$_q$-phenyl, where said pyridyl, said pyrimidyl, and said phenyl moieties are optionally substituted with one, two or three substituents each independently selected from halo, (C$_1$-C$_4$)alkoxy, cyano, —NH$_2$, (C$_1$-C$_4$)alkyl-NH—, ((C$_1$-C$_4$)alkyl)$_2$-N—, —(CH$_2$)—OH, —C(O)—NH$_2$, —C(O)—NH—(C$_1$-C$_4$)alkyl, —C(O)—N((C$_1$-C$_4$)alkyl)$_2$, —C(O)—NH—(CH$_2$)$_p$—OH, —(CH$_2$)—NH$_2$, —(CH$_2$)—NH—C(O)CH$_3$ and —(CH$_2$)—NH—C(O)H;

p is 1 or 2, and q is 0 or 1.

2. A compound of formula (I), or a salt thereof, according to claim 1 wherein R$^1$ is a phenyl substituted with one or two substituents each independently selected from halo and (C$_1$-C$_4$)alkyl.

3. A compound of formula (I), or a salt thereof, according to claim 1 wherein R$^1$ is a 6-oxo-1,6-dihydropyridin-3-yl having Formula (Ia) or a 2-oxo-1,2-dihydropyridin-3-yl having Formula (Ib),

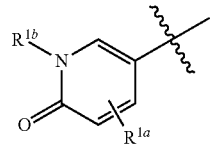

wherein R$^{1a}$ is halo and R$^{1b}$ is H or (C$_1$-C$_4$)alkyl.

4. A compound of formula (I), or a salt thereof, according to claim 1 wherein R$^2$ is selected from p-chlorophenyl, p-cyanophenyl, o-methyl-p-chlorophenyl, p-fluoro-m-chlorophenyl and m-fluoro-p-chlorophenyl.

5. A compound of formula (I), or a salt thereof, according to claim 1 wherein $R^3$ is isopropyl.

6. A compound of formula (I), or a salt thereof, according to claim 1 wherein $R^4$ is selected from $—(CH_2)_q$-pyridyl, $—(CH_2)_q$-pyrimidyl and $—(CH_2)_q$-phenyl, where said pyridyl, said pyrimidyl, and said phenyl moieties are optionally substituted with one or two substituents each independently selected from $(C_1-C_4)$alkoxy, $((C_1-C_4)$alkyl$)_2$-N—, $—C(O)—NH—(C_1-C_4)$alkyl and $—C(O)—N((C_1-C_4)$alkyl$)_2$ where q is 0 or 1.

7. A compound of formula (I), or a salt thereof, according to claim 1 wherein $R^4$ is selected from

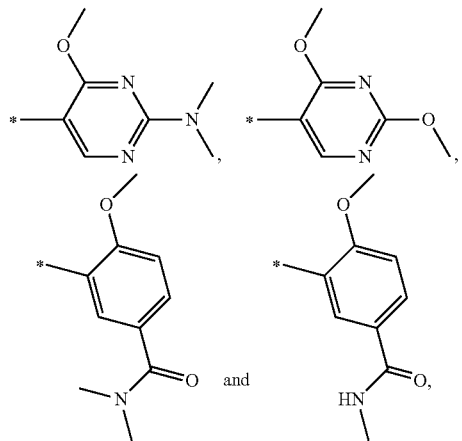

where * indicates the point of attachment to the remainder of the molecule.

8. A compound of formula (I), or a salt thereof, according to claim 1 wherein $R^4$ is

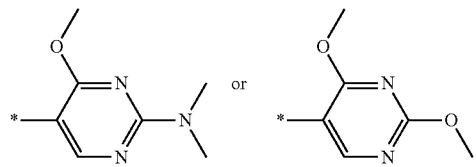 [SMILES: *c1cnc(N(C)C)nc1OC ; *c1cnc(OC)nc1OC]

where * indicates the point of attachment to the remainder of the molecule.

9. A compound of formula (I) according to claim 1 selected from:
 1-(3-Chloro-2-fluorophenyl)-6-(4-chlorophenyl)-7-isopropyl-8-(2-methoxyphenyl)-6,7-dihydro-1H-purin-2(3H)-one;
 1-(3-Chloro-2-fluorophenyl)-6-(4-chloro-2-methylphenyl)-7-isopropyl-8-(2-methoxyphenyl)-6,7-dihydro-1H-purin-2(3H)-one;
 6-(4-Chloro-2-methylphenyl)-1-(5-chloro-2-methylphenyl)-7-isopropyl-8-(2-methoxyphenyl)-6,7-dihydro-1H-purin-2(3H)-one;
 6-(4-Chloro-2-methylphenyl)-1-(5-chloro-2-methylphenyl)-7-isopropyl-8-(4-methoxypyridin-3-yl)-6,7-dihydro-1H-purin-2(3H)-one;
 8-Bromo-1-(3-chloro-2-fluorophenyl)-6-(4-chlorophenyl)-7-isopropyl-6,7-dihydro-1H-purin-2(3H)-one;
 1-(3-Chloro-2-fluorophenyl)-6-(4-chlorophenyl)-7-isopropyl-8-(4-methoxypyridin-3-yl)-6,7-dihydro-1H-purin-2(3H)-one;
 6-(4-Chloro-2-methylphenyl)-1-(5-chloro-2-methylphenyl)-8-(5-fluoro-2-methoxyphenyl)-7-isopropyl-6,7-dihydro-1H-purin-2(3H)-one;
 3-(6-(4-Chloro-2-methylphenyl)-1-(5-chloro-2-methylphenyl)-7-isopropyl-2-oxo-2,3,6,7-tetrahydro-1H-purin-8-yl)-N-(2-hydroxyethyl)-4-methoxybenzamide;
 3-(6-(4-Chloro-2-methylphenyl)-1-(5-chloro-2-methylphenyl)-7-isopropyl-2-oxo-2,3,6,7-tetrahydro-1H-purin-8-yl)-4-methoxy-N-methylbenzamide;
 3-(6-(4-Chloro-2-methylphenyl)-1-(5-chloro-2-methylphenyl)-7-isopropyl-2-oxo-2,3,6,7-tetrahydro-1H-purin-8-yl)-4-methoxy-N,N-dimethylbenzamide;
 6-(4-Chloro-2-methylphenyl)-1-(5-chloro-2-methylphenyl)-8-(5-(hydroxymethyl)-2-methoxyphenyl)-7-isopropyl-6, 7-dihydro-1H-purin-2(3H)-one;
 3-(6-(4-Chloro-2-methylphenyl)-1-(5-chloro-2-methylphenyl)-7-isopropyl-2-oxo-2,3,6,7-tetrahydro-1H-purin-8-yl)-4-methoxybenzonitrile;
 4-(1-(5-Chloro-2-methylphenyl)-7-isopropyl-8-(2-methoxyphenyl)-2-oxo-2,3,6,7-tetrahydro-1H-purin-6-yl)benzonitrile; and
 4-(1-(3-Chloro-2-fluorophenyl)-7-isopropyl-8-(2-methoxyphenyl)-2-oxo-2,3, 6,7-tetrahydro-1H-purin-6-yl)benzonitrile;
 6-(4-Chloro-3-fluorophenyl)-1-(3-chloro-4-fluorophenyl)-8-(2,4-dimethoxypyrimidin-5-yl)-7-isopropyl-6,7-dihydro-1H-purin-2(3H)-one;
 1-(5-Chloro-1-methyl-6-oxo-1,6-dihydropyridin-3-yl)-6-(4-chloro-2-methylphenyl)-8-(2,4-dimethoxypyrimidin-5-yl)-7-isopropyl-6,7-dihydro-1H-purin-2(3H)-one;
 1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;
 1-(5-Chloro-1-methyl-2-oxo-1,2-dihydropyridin-3-yl)-6-(4-chlorophenyl)-8-(2,4-dimethoxypyrimidin-5-yl)-7-isopropyl-6,7-dihydro-1H-purin-2(3H)-one;
 1-(5-Chloro-1-methyl-6-oxo-1,6-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;
 1-(5-Chloro-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one;
 8-(2-Amino-4-methoxypyrimidin-5-yl)-1-(5-chloro-1-methyl-2-oxo-1,2-dihydropyridin-3-yl)-6-(4-chlorophenyl)-7-isopropyl-6,7-dihydro-1H-purin-2(3H)-one;
 1-(5-Chloro-1-methyl-2-oxo-1,2-dihydropyridin-3-yl)-6-(4-chlorophenyl)-8-(2-(dimethylamino)-4-methoxypyrimidin-5-yl)-7-isopropyl-6,7-dihydro-1H-purin-2 (3H)-one;
 6-(4-Chloro-3-fluorophenyl)-1-(3-chloro-4-fluorophenyl)-8-(2-(dimethylamino)-4-methoxypyrimidin-5-yl)-7-isopropyl-6,7-dihydro-1H-purin-2(3H)-one;
 1-(5-Chloro-1-methyl-2-oxo-1,2-dihydropyridin-3-yl)-6-(4-chloro-3-fluorophenyl)-8-(2-(dimethylamino)-4-methoxypyrimidin-5-yl)-7-isopropyl-6,7-dihydro-1H-purin-2(3H)-one; and
 1-(5-Chloro-2-oxo-1,2-dihydropyridin-3-yl)-6-(4-chloro-3-fluorophenyl)-8-(2,4-dimethoxypyrimidin-5-yl)-7-isopropyl-6,7-dihydro-1H-purin-2(3H)-one;
or a salt thereof.

10. A pharmaceutical composition comprising a therapeutically effective amount of a compound of formula (I) or salt thereof according to claim 1, and one or more pharmaceutically acceptable carriers.

* * * * *